United States Patent
Alexander et al.

(10) Patent No.: US 8,435,507 B2
(45) Date of Patent: May 7, 2013

(54) PROSTATE-SPECIFIC ANTIGEN-DERIVED MHC CLASS II RESTRICTED PEPTIDES AND THEIR USE IN VACCINES TO TREAT OR PREVENT PROSTATE CANCER

(75) Inventors: Richard B. Alexander, Ellicott City, MD (US); Elena N. Klyushnenkova, Baltimore, MD (US); Jason Link, Portland, OR (US); Arthur Vandenbark, Portland, OR (US)

(73) Assignees: University of Maryland, Baltimore, MD (US); The United States of America as Represented by the Dept of Veterans Affairs, Washington, DC (US); Oregon Health & Science University, Portland, OR (US)

( * ) Notice: Subject to any disclaimer, the term of this patent is extended or adjusted under 35 U.S.C. 154(b) by 990 days.

(21) Appl. No.: 11/573,667

(22) PCT Filed: Aug. 19, 2005

(86) PCT No.: PCT/US2005/029320
§ 371 (c)(1),
(2), (4) Date: May 20, 2008

(87) PCT Pub. No.: WO2006/023598
PCT Pub. Date: Mar. 2, 2006

(65) Prior Publication Data
US 2008/0260760 A1    Oct. 23, 2008

Related U.S. Application Data

(60) Provisional application No. 60/602,630, filed on Aug. 19, 2004.

(51) Int. Cl.
*A61K 48/00* (2006.01)
*C12P 19/34* (2006.01)

(52) U.S. Cl.
USPC ............................. 424/93.2; 435/91.1

(58) Field of Classification Search ............... 424/93.2; 435/91.1
See application file for complete search history.

(56) References Cited

U.S. PATENT DOCUMENTS

| 5,788,963 A | 8/1998 | Murphy et al. |
| 6,034,218 A | 3/2000 | Reed et al. |
| 6,664,377 B1 | 12/2003 | Xu et al. |
| 2005/0220807 A1 * | 10/2005 | Lu et al. ............... 424/190.1 |

FOREIGN PATENT DOCUMENTS

| WO | WO9735021 A | * | 9/1997 |
| WO | WO 0160860 | * | 8/2001 |

OTHER PUBLICATIONS

Castleden et al (Hum Gene Ther, 20;8(17):2087-102, 1997).*
Richard B. Alexander, et al., vol. 171, 2326-2329, Jun. 2004, *Granulomatous prostatitis* linked to HLA-DRB1*1501.
J. M. Corman, Recognition of prostate-specific antigenic peptide determinants by human CD4 and CD8 T cells, Clin Exp Immunol 1998; 114:166-172.

* cited by examiner

*Primary Examiner* — Gerald Leffers, Jr.
*Assistant Examiner* — Magdalene Sgagias
(74) *Attorney, Agent, or Firm* — Evans & Molinelli PLLC; Judith A. Evans

(57) ABSTRACT

The present invention relates to immunogenic peptides derived from human prostate cancer antigen (PSA-derived peptides) and their use as vaccines to treat or prevent prostate cancer. The invention is also related to dendritic cells from a patient having prostate cancer, which dendritic cells have been exposed to one or more PSA-derived peptides, and their use to treat or prevent prostate cancer in the patient. The invention is also directed to T-cells from a patient which cells are specific for PSA-activated peptide(s), and their uses to treat or prevent prostate cancer.

6 Claims, 17 Drawing Sheets

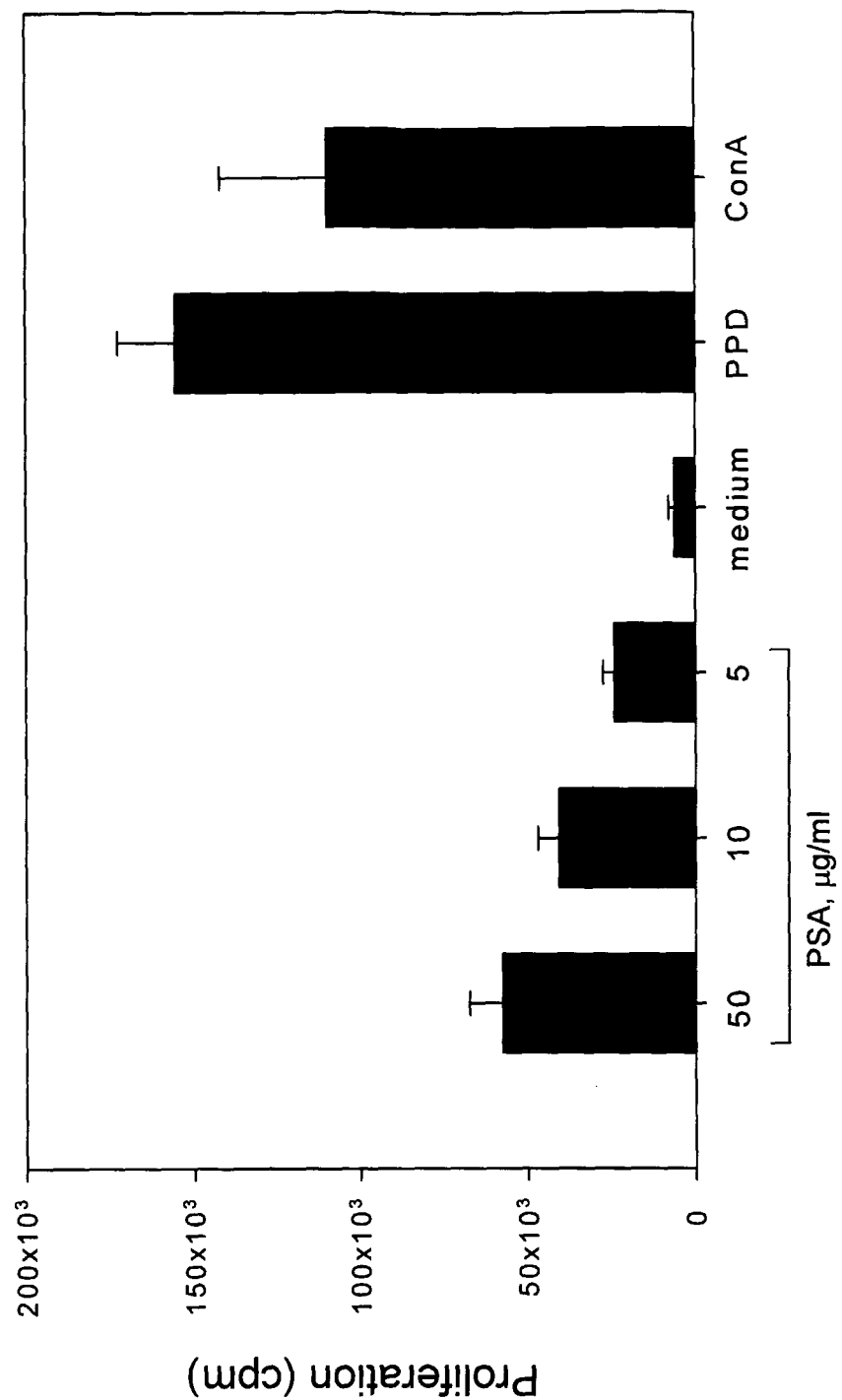

FIG.1B

```
MWVPVVFLTL
         (11-30)
SVTWIGAAPL ILSRIVGGWE
                    (31-50)
                    CEKHSQPWQV LVASRGRAVC
                                        (51-70)
                                        GGVLVHPQWV LTAAHCIRNK
         (21-40)
                              (41-60)
                                                  (61-80)

(81-100)
                    SVILLGRHSL FHPEDTGQVF
                                        (101-120)
                                        QVSHSFPHPL YDMSLLKNRF
                                                            (121-140)
                                                            LRPGDDSSHD LMLLRLSEPA
         (71-90)
                              (91-110)
                                                  (111-130)

(131-150)
                    ELTDAVKVMD LPTQEPALGT
                                        (151-170)
                                        TCYASGWGSI EPEEFLTPKK
                                                            (171-190)
                                                            LQCVDLHVIS NDVCAQVHPQ
                              (141-160)
                                                  (161-180)      [169-181]
                                                                          (181-200)

(191-210)
                    KVTKFMLCAG RWTGGKSTCS
                                        (211-230)
                                        GDSGGPLVCN GVLQGITSWG
                                                            (231-250)
                                                            SEPCALPERP SLYTKVVHYR
                              (201-220)
                                                  (221-240)      [221-233]
                                                                          (241-261)

KWIKDTIVAN P
```

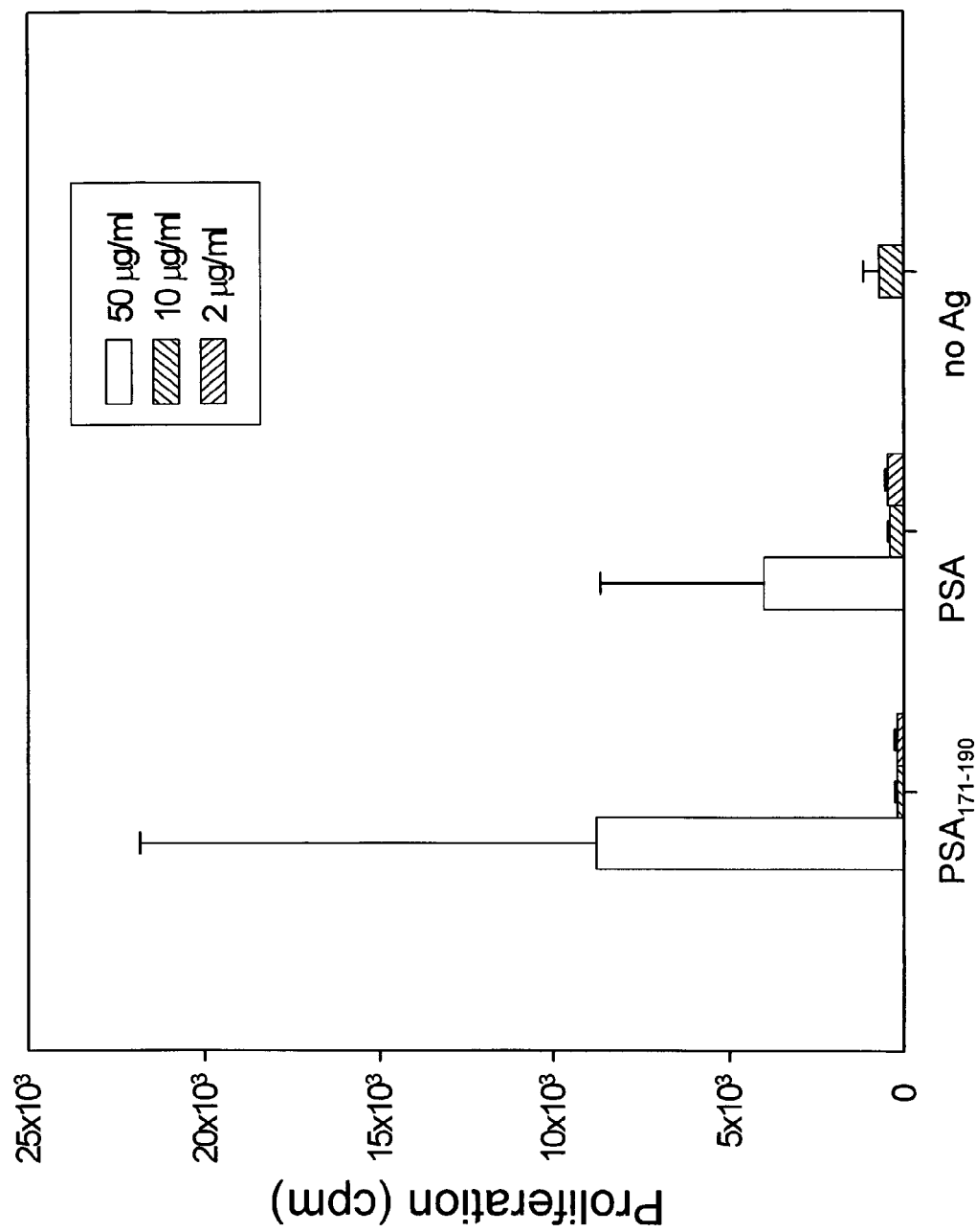

SEQUENCE LISTING

<160> NUMBER OF SEQ ID NOS: 92

<210> SEQ ID NO 1
<211> LENGTH: 60
<212> TYPE: DNA
<213> ORGANISM: Homo sapiens

<400> SEQUENCE: 1
cttcagtgtg tggacctcca tgttatttcc aatgacgtgt gtgcgcaagt tcaccctcag    60

<210> SEQ ID NO 2
<211> LENGTH: 20
<212> TYPE: PRT
<213> ORGANISM: Homo sapiens

<400> SEQUENCE: 2

Leu Gln Cys Val Asp Leu His Val Ile Ser Asn Asp Val Cys Ala Gln
1               5                   10                  15

Val His Pro Gln
            20

<210> SEQ ID NO 3
<211> LENGTH: 60
<212> TYPE: DNA
<213> ORGANISM: Homo sapiens

<400> SEQUENCE: 3
ggtgtgcttc aaggtatcac gtcatggggc agtgaaccat gtgccctgcc cgaaaggcct    60

<210> SEQ ID NO 4
<211> LENGTH: 20
<212> TYPE: PRT
<213> ORGANISM: Homo sapiens

<400> SEQUENCE: 4

Gly Val Leu Gln Gly Ile Thr Ser Trp Gly Ser Glu Pro Cys Ala Leu
1               5                   10                  15

Pro Glu Arg Pro
            20

<210> SEQ ID NO 5
<211> LENGTH: 39
<212> TYPE: DNA
<213> ORGANISM: Homo sapiens

<400> SEQUENCE: 5
aagaaacttc agtgtgtgga cctccatgtt atttccaat                           39

<210> SEQ ID NO 6
<211> LENGTH: 13
<212> TYPE: PRT
<213> ORGANISM: Homo sapiens

<400> SEQUENCE: 6

Lys Lys Leu Gln Cys Val Asp Leu His Val Ile Ser Asn
1               5                   10

<210> SEQ ID NO 7
<211> LENGTH: 39
<212> TYPE: DNA
<213> ORGANISM: Homo sapiens

<400> SEQUENCE: 7

```
ggtgtgcttc aaggtatcac gtcatggggc agtgaacca                              39
```

<210> SEQ ID NO 8
<211> LENGTH: 13
<212> TYPE: PRT
<213> ORGANISM: Homo sapiens

<400> SEQUENCE: 8

Gly Val Leu Gln Gly Ile Thr Ser Trp Gly Ser Glu Pro
1               5                   10

<210> SEQ ID NO 9
<211> LENGTH: 27
<212> TYPE: DNA
<213> ORGANISM: Homo sapiens

<400> SEQUENCE: 9

```
cttcagtgtg tggacctcca tgttatt                                          27
```

<210> SEQ ID NO 10
<211> LENGTH: 9
<212> TYPE: PRT
<213> ORGANISM: Homo sapiens

<400> SEQUENCE: 10

Leu Gln Cys Val Asp Leu His Val Ile
1               5

<210> SEQ ID NO 11
<211> LENGTH: 27
<212> TYPE: DNA
<213> ORGANISM: Homo sapiens

<400> SEQUENCE: 11

```
cttcaaggta tcacgtcatg gggcagt                                          27
```

<210> SEQ ID NO 12
<211> LENGTH: 9
<212> TYPE: PRT
<213> ORGANISM: Homo sapiens

<400> SEQUENCE: 12

Leu Gln Gly Ile Thr Ser Trp Gly Ser
1               5

<210> SEQ ID NO 13
<211> LENGTH: 19
<212> TYPE: PRT
<213> ORGANISM: Homo sapiens

<400> SEQUENCE: 13

Leu Gln Cys Val Asp Leu His Val Ile Ser Asn Asp Val Cys Ala Gln
1               5                   10                  15

Val His Pro

<210> SEQ ID NO 14
<211> LENGTH: 18
<212> TYPE: PRT
<213> ORGANISM: Homo sapiens

<400> SEQUENCE: 14

Leu Gln Cys Val Asp Leu His Val Ile Ser Asn Asp Val Cys Ala Gln
1               5                   10                  15

Val His

<210> SEQ ID NO 15
<211> LENGTH: 17
<212> TYPE: PRT
<213> ORGANISM: Homo sapiens

<400> SEQUENCE: 15

Leu Gln Cys Val Asp Leu His Val Ile Ser Asn Asp Val Cys Ala Gln
1               5                   10                  15

Val

<210> SEQ ID NO 16
<211> LENGTH: 16
<212> TYPE: PRT
<213> ORGANISM: Homo sapiens

<400> SEQUENCE: 16

Leu Gln Cys Val Asp Leu His Val Ile Ser Asn Asp Val Cys Ala Gln
1               5                   10                  15

<210> SEQ ID NO 17
<211> LENGTH: 15
<212> TYPE: PRT
<213> ORGANISM: Homo sapiens

<400> SEQUENCE: 17

Leu Gln Cys Val Asp Leu His Val Ile Ser Asn Asp Val Cys Ala
1               5                   10                  15

<210> SEQ ID NO 18
<211> LENGTH: 15
<212> TYPE: PRT
<213> ORGANISM: Homo sapiens

<400> SEQUENCE: 18

Leu Gln Cys Val Asp Leu His Val Ile Ser Asn Asp Val Cys Ala
1               5                   10                  15

<210> SEQ ID NO 19
<211> LENGTH: 13
<212> TYPE: PRT
<213> ORGANISM: Homo sapiens

<400> SEQUENCE: 19

Leu Gln Cys Val Asp Leu His Val Ile Ser Asn Asp Val
1               5                   10

<210> SEQ ID NO 20
<211> LENGTH: 12
<212> TYPE: PRT
<213> ORGANISM: Homo sapiens

<400> SEQUENCE: 20

Leu Gln Cys Val Asp Leu His Val Ile Ser Asn Asp
1               5                   10

<210> SEQ ID NO 21
<211> LENGTH: 11
<212> TYPE: PRT
<213> ORGANISM: Homo sapiens

<400> SEQUENCE: 21

Leu Gln Cys Val Asp Leu His Val Ile Ser Asn
1               5                   10

```
<210> SEQ ID NO 22
<211> LENGTH: 10
<212> TYPE: PRT
<213> ORGANISM: Homo sapiens

<400> SEQUENCE: 22

Leu Gln Cys Val Asp Leu His Val Ile Ser
1               5                   10

<210> SEQ ID NO 23
<211> LENGTH: 9
<212> TYPE: PRT
<213> ORGANISM: Homo sapiens

<400> SEQUENCE: 23

Leu Gln Cys Val Asp Leu His Val Ile
1               5

<210> SEQ ID NO 24
<211> LENGTH: 19
<212> TYPE: PRT
<213> ORGANISM: Homo sapiens

<400> SEQUENCE: 24

Gly Val Leu Gln Gly Ile Thr Ser Trp Gly Ser Glu Pro Cys Ala Leu
1               5                   10                  15

Pro Glu Arg

<210> SEQ ID NO 25
<211> LENGTH: 18
<212> TYPE: PRT
<213> ORGANISM: Homo sapiens

<400> SEQUENCE: 25

Gly Val Leu Gln Gly Ile Thr Ser Trp Gly Ser Glu Pro Cys Ala Leu
1               5                   10                  15

Pro Glu

<210> SEQ ID NO 26
<211> LENGTH: 17
<212> TYPE: PRT
<213> ORGANISM: Homo sapiens

<400> SEQUENCE: 26

Gly Val Leu Gln Gly Ile Thr Ser Trp Gly Ser Glu Pro Cys Ala Leu
1               5                   10                  15

Pro

<210> SEQ ID NO 27
<211> LENGTH: 16
<212> TYPE: PRT
<213> ORGANISM: Homo sapiens

<400> SEQUENCE: 27

Gly Val Leu Gln Gly Ile Thr Ser Trp Gly Ser Glu Pro Cys Ala Leu
1               5                   10                  15

<210> SEQ ID NO 28
<211> LENGTH: 15
<212> TYPE: PRT
<213> ORGANISM: Homo sapiens

<400> SEQUENCE: 28
```

Gly Val Leu Gln Gly Ile Thr Ser Trp Gly Ser Glu Pro Cys Ala
1               5                   10                  15

<210> SEQ ID NO 29
<211> LENGTH: 14
<212> TYPE: PRT
<213> ORGANISM: Homo sapiens

<400> SEQUENCE: 29

Gly Val Leu Gln Gly Ile Thr Ser Trp Gly Ser Glu Pro Cys
1               5                   10

<210> SEQ ID NO 30
<211> LENGTH: 13
<212> TYPE: PRT
<213> ORGANISM: Homo sapiens

<400> SEQUENCE: 30

Gly Val Leu Gln Gly Ile Thr Ser Trp Gly Ser Glu Pro
1               5                   10

<210> SEQ ID NO 31
<211> LENGTH: 12
<212> TYPE: PRT
<213> ORGANISM: Homo sapiens

<400> SEQUENCE: 31

Gly Val Leu Gln Gly Ile Thr Ser Trp Gly Ser Glu
1               5                   10

<210> SEQ ID NO 32
<211> LENGTH: 11
<212> TYPE: PRT
<213> ORGANISM: Homo sapiens

<400> SEQUENCE: 32

Gly Val Leu Gln Gly Ile Thr Ser Trp Gly Ser
1               5                   10

<210> SEQ ID NO 33
<211> LENGTH: 10
<212> TYPE: PRT
<213> ORGANISM: Homo sapiens

<400> SEQUENCE: 33

Gly Val Leu Gln Gly Ile Thr Ser Trp Gly
1               5                   10

<210> SEQ ID NO 34
<211> LENGTH: 9
<212> TYPE: PRT
<213> ORGANISM: Homo sapiens

<400> SEQUENCE: 34

Gly Val Leu Gln Gly Ile Thr Ser Trp
1               5

<210> SEQ ID NO 35
<211> LENGTH: 19
<212> TYPE: PRT
<213> ORGANISM: Homo sapiens

<400> SEQUENCE: 35

Val Leu Gln Gly Ile Thr Ser Trp Gly Ser Glu Pro Cys Ala Leu Pro
1               5                   10                  15

Glu Arg Pro

<210> SEQ ID NO 36
<211> LENGTH: 18
<212> TYPE: PRT
<213> ORGANISM: Homo sapiens

<400> SEQUENCE: 36

Leu Gln Gly Ile Thr Ser Trp Gly Ser Glu Pro Cys Ala Leu Pro Glu
1               5                   10                  15

Arg Pro

<210> SEQ ID NO 37
<211> LENGTH: 17
<212> TYPE: PRT
<213> ORGANISM: Homo sapiens

<400> SEQUENCE: 37

Gln Gly Ile Thr Ser Trp Gly Ser Glu Pro Cys Ala Leu Pro Glu Arg
1               5                   10                  15

Pro

<210> SEQ ID NO 38
<211> LENGTH: 16
<212> TYPE: PRT
<213> ORGANISM: Homo sapiens

<400> SEQUENCE: 38

Gly Ile Thr Ser Trp Gly Ser Glu Pro Cys Ala Leu Pro Glu Arg Pro
1               5                   10                  15

<210> SEQ ID NO 39
<211> LENGTH: 15
<212> TYPE: PRT
<213> ORGANISM: Homo sapiens

<400> SEQUENCE: 39

Ile Thr Ser Trp Gly Ser Glu Pro Cys Ala Leu Pro Glu Arg Pro
1               5                   10                  15

<210> SEQ ID NO 40
<211> LENGTH: 14
<212> TYPE: PRT
<213> ORGANISM: Homo sapiens

<400> SEQUENCE: 40

Thr Ser Trp Gly Ser Glu Pro Cys Ala Leu Pro Glu Arg Pro
1               5                   10

<210> SEQ ID NO 41
<211> LENGTH: 13
<212> TYPE: PRT
<213> ORGANISM: Homo sapiens

<400> SEQUENCE: 41

Ser Trp Gly Ser Glu Pro Cys Ala Leu Pro Glu Arg Pro
1               5                   10

<210> SEQ ID NO 42
<211> LENGTH: 12
<212> TYPE: PRT
<213> ORGANISM: Homo sapiens

<400> SEQUENCE: 42

```
Trp Gly Ser Glu Pro Cys Ala Leu Pro Glu Arg Pro
1               5                   10
```

<210> SEQ ID NO 43
<211> LENGTH: 11
<212> TYPE: PRT
<213> ORGANISM: Homo sapiens

<400> SEQUENCE: 43

```
Gly Ser Glu Pro Cys Ala Leu Pro Glu Arg Pro
1               5                   10
```

<210> SEQ ID NO 44
<211> LENGTH: 10
<212> TYPE: PRT
<213> ORGANISM: Homo sapiens

<400> SEQUENCE: 44

```
Ser Glu Pro Cys Ala Leu Pro Glu Arg Pro
1               5                   10
```

<210> SEQ ID NO 45
<211> LENGTH: 9
<212> TYPE: PRT
<213> ORGANISM: Homo sapiens

<400> SEQUENCE: 45

```
Glu Pro Cys Ala Leu Pro Glu Arg Pro
1               5
```

<210> SEQ ID NO 46
<211> LENGTH: 9
<212> TYPE: PRT
<213> ORGANISM: Artificial Sequence
<220> FEATURE:
<223> OTHER INFORMATION: Synthetic construct

<400> SEQUENCE: 46

```
Leu Gln Gly Ile Thr Ser Trp Gly Ser
1               5
```

<210> SEQ ID NO 47
<211> LENGTH: 10
<212> TYPE: PRT
<213> ORGANISM: Homo sapiens

<400> SEQUENCE: 47

```
Val Leu Gln Gly Ile Thr Ser Trp Gly Ser
1               5                   10
```

<210> SEQ ID NO 48
<211> LENGTH: 11
<212> TYPE: PRT
<213> ORGANISM: Homo sapiens

<400> SEQUENCE: 48

```
Gly Val Leu Gln Gly Ile Thr Ser Trp Gly Ser
1               5                   10
```

<210> SEQ ID NO 49
<211> LENGTH: 12
<212> TYPE: PRT
<213> ORGANISM: Homo sapiens

<400> SEQUENCE: 49

```
Asn Gly Val Leu Gln Gly Ile Thr Ser Trp Gly Ser
1               5                   10
```

```
<210> SEQ ID NO 50
<211> LENGTH: 10
<212> TYPE: PRT
<213> ORGANISM: Homo sapiens

<400> SEQUENCE: 50

Leu Gln Gly Ile Thr Ser Trp Gly Ser Glu
1               5                   10
```

```
<210> SEQ ID NO 51
<211> LENGTH: 11
<212> TYPE: PRT
<213> ORGANISM: Homo sapiens

<400> SEQUENCE: 51

Val Leu Gln Gly Ile Thr Ser Trp Gly Ser Glu
1               5                   10
```

```
<210> SEQ ID NO 52
<211> LENGTH: 12
<212> TYPE: PRT
<213> ORGANISM: Homo sapiens

<400> SEQUENCE: 52

Gly Val Leu Gln Gly Ile Thr Ser Trp Gly Ser Glu
1               5                   10
```

```
<210> SEQ ID NO 53
<211> LENGTH: 13
<212> TYPE: PRT
<213> ORGANISM: Homo sapiens

<400> SEQUENCE: 53

Asn Gly Val Leu Gln Gly Ile Thr Ser Trp Gly Ser Glu
1               5                   10
```

```
<210> SEQ ID NO 54
<211> LENGTH: 11
<212> TYPE: PRT
<213> ORGANISM: Homo sapiens

<400> SEQUENCE: 54

Leu Gln Gly Ile Thr Ser Trp Gly Ser Glu Pro
1               5                   10
```

```
<210> SEQ ID NO 55
<211> LENGTH: 12
<212> TYPE: PRT
<213> ORGANISM: Homo sapiens

<400> SEQUENCE: 55

Val Leu Gln Gly Ile Thr Ser Trp Gly Ser Glu Pro
1               5                   10
```

```
<210> SEQ ID NO 56
<211> LENGTH: 13
<212> TYPE: PRT
<213> ORGANISM: Homo sapiens

<400> SEQUENCE: 56

Gly Val Leu Gln Gly Ile Thr Ser Trp Gly Ser Glu Pro
1               5                   10
```

```
<210> SEQ ID NO 57
<211> LENGTH: 14
<212> TYPE: PRT
<213> ORGANISM: Homo sapiens

<400> SEQUENCE: 57

Asn Gly Val Leu Gln Gly Ile Thr Ser Trp Gly Ser Glu Pro
1               5                   10

<210> SEQ ID NO 58
<211> LENGTH: 12
<212> TYPE: PRT
<213> ORGANISM: Homo sapiens

<400> SEQUENCE: 58

Leu Gln Gly Ile Thr Ser Trp Gly Ser Glu Pro Cys
1               5                   10

<210> SEQ ID NO 59
<211> LENGTH: 13
<212> TYPE: PRT
<213> ORGANISM: Homo sapiens

<400> SEQUENCE: 59

Val Leu Gln Gly Ile Thr Ser Trp Gly Ser Glu Pro Cys
1               5                   10

<210> SEQ ID NO 60
<211> LENGTH: 14
<212> TYPE: PRT
<213> ORGANISM: Homo sapiens

<400> SEQUENCE: 60

Gly Val Leu Gln Gly Ile Thr Ser Trp Gly Ser Glu Pro Cys
1               5                   10

<210> SEQ ID NO 61
<211> LENGTH: 15
<212> TYPE: PRT
<213> ORGANISM: Homo sapiens

<400> SEQUENCE: 61

Asn Gly Val Leu Gln Gly Ile Thr Ser Trp Gly Ser Glu Pro Cys
1               5                   10                  15

<210> SEQ ID NO 62

<400> SEQUENCE: 62

000 000 000 000 000

<210> SEQ ID NO 63
<211> LENGTH: 9
<212> TYPE: PRT
<213> ORGANISM: Artificial Sequence
<220> FEATURE:
<223> OTHER INFORMATION: Synthetic construct

<400> SEQUENCE: 63

Leu Arg Cys Val Asp Leu His Val Ile
1               5

<210> SEQ ID NO 64
<211> LENGTH: 9
<212> TYPE: PRT
<213> ORGANISM: Artificial Sequence
```

```
<220> FEATURE:
<223> OTHER INFORMATION: Synthetic construct

<400> SEQUENCE: 64

Leu Val Cys Val Asp Leu His Val Ile
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic construct

<400> SEQUENCE: 65

Leu Gln Ile Val Asp Leu His Val Ile
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic construct

<400> SEQUENCE: 66

Leu Gln Cys Tyr Asp Leu His Val Ile
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic construct

<400> SEQUENCE: 67

Leu Gln Cys Phe Asp Leu His Val Ile
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic construct

<400> SEQUENCE: 68

Leu Gln Cys Val Asp Arg His Val Ile
1               5

<210> SEQ ID NO 69

<400> SEQUENCE: 69

000 000 000 000 000

<210> SEQ ID NO 70
<211> LENGTH: 9
<212> TYPE: PRT
<213> ORGANISM: Artificial Sequence
<220> FEATURE:
<223> OTHER INFORMATION: Synthetic construct

<400> SEQUENCE: 70

Leu Arg Gly Ile Thr Ser Trp Gly Ser
1               5
```

```
<210> SEQ ID NO 71
<211> LENGTH: 9
<212> TYPE: PRT
<213> ORGANISM: Artificial Sequence
<220> FEATURE:
<223> OTHER INFORMATION: Synthetic construct

<400> SEQUENCE: 71

Leu Gln Ile Ile Thr Ser Trp Gly Ser
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic construct

<400> SEQUENCE: 72

Leu Gln Leu Ile Thr Ser Trp Gly Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic construct

<400> SEQUENCE: 73

Leu Gln Gly Tyr Thr Ser Trp Gly Ser
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic construct

<400> SEQUENCE: 74

Leu Gln Gly Phe Thr Ser Trp Gly Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic construct

<400> SEQUENCE: 75

Leu Gln Gly Ile Thr Arg Trp Gly Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic construct

<400> SEQUENCE: 76

Leu Gln Gly Ile Thr Ser Leu Gly Ser
1               5

<210> SEQ ID NO 77
```

```
<211> LENGTH: 9
<212> TYPE: PRT
<213> ORGANISM: Artificial Sequence
<220> FEATURE:
<223> OTHER INFORMATION: Synthetic construct

<400> SEQUENCE: 77

Leu Gln Gly Ile Thr Ser Met Gly Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic construct

<400> SEQUENCE: 78

Leu Gln Gly Ile Thr Ser Phe Gly Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic construct

<400> SEQUENCE: 79

Leu Gln Gly Ile Thr Ser Trp Gly Leu
1               5

<210> SEQ ID NO 80
<211> LENGTH: 18
<212> TYPE: PRT
<213> ORGANISM: Homo sapiens

<400> SEQUENCE: 80

Gln Cys Val Asp Leu His Val Ile Ser Asn Asp Val Cys Ala Gln Val
1               5                   10                  15

His Pro

<210> SEQ ID NO 81
<211> LENGTH: 17
<212> TYPE: PRT
<213> ORGANISM: Homo sapiens

<400> SEQUENCE: 81

Cys Val Asp Leu His Val Ile Ser Asn Asp Val Cys Ala Gln Val His
1               5                   10                  15

Pro

<210> SEQ ID NO 82
<211> LENGTH: 16
<212> TYPE: PRT
<213> ORGANISM: Homo sapiens

<400> SEQUENCE: 82

Val Asp Leu His Val Ile Ser Asn Asp Val Cys Ala Gln Val His Pro
1               5                   10                  15

<210> SEQ ID NO 83
<211> LENGTH: 15
<212> TYPE: PRT
<213> ORGANISM: Homo sapiens
```

<400> SEQUENCE: 83

Asp Leu His Val Ile Ser Asn Asp Val Cys Ala Gln Val His Pro
1               5                   10                  15

<210> SEQ ID NO 84
<211> LENGTH: 14
<212> TYPE: PRT
<213> ORGANISM: Homo sapiens

<400> SEQUENCE: 84

Leu His Val Ile Ser Asn Asp Val Cys Ala Gln Val His Pro
1               5                   10

<210> SEQ ID NO 85
<211> LENGTH: 13
<212> TYPE: PRT
<213> ORGANISM: Homo sapiens

<400> SEQUENCE: 85

His Val Ile Ser Asn Asp Val Cys Ala Gln Val His Pro
1               5                   10

<210> SEQ ID NO 86
<211> LENGTH: 12
<212> TYPE: PRT
<213> ORGANISM: Homo sapiens

<400> SEQUENCE: 86

Val Ile Ser Asn Asp Val Cys Ala Gln Val His Pro
1               5                   10

<210> SEQ ID NO 87
<211> LENGTH: 11
<212> TYPE: PRT
<213> ORGANISM: Homo sapiens

<400> SEQUENCE: 87

Ile Ser Asn Asp Val Cys Ala Gln Val His Pro
1               5                   10

<210> SEQ ID NO 88
<211> LENGTH: 10
<212> TYPE: PRT
<213> ORGANISM: Homo sapiens

<400> SEQUENCE: 88

Ser Asn Asp Val Cys Ala Gln Val His Pro
1               5                   10

<210> SEQ ID NO 89
<211> LENGTH: 9
<212> TYPE: PRT
<213> ORGANISM: Homo sapiens

<400> SEQUENCE: 89

Asn Asp Val Cys Ala Gln Val His Pro
1               5

<210> SEQ ID NO 90
<211> LENGTH: 8
<212> TYPE: PRT
<213> ORGANISM: Homo sapiens

<400> SEQUENCE: 90

Asp Val Cys Ala Gln Val His Pro

```
<210> SEQ ID NO 91
<211> LENGTH: 9
<212> TYPE: PRT
<213> ORGANISM: Artificial Sequence
<220> FEATURE:
<223> OTHER INFORMATION: Synthetic construct

<400> SEQUENCE: 91

Leu Gln Cys Val Asp Leu Leu Val Ile
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic construct

<400> SEQUENCE: 92

Leu Gln Cys Val Asp Leu Met Val Ile
1               5
```

PROSTATE-SPECIFIC ANTIGEN-DERIVED MHC CLASS II RESTRICTED PEPTIDES AND THEIR USE IN VACCINES TO TREAT OR PREVENT PROSTATE CANCER

CROSS-REFERENCE TO RELATED APPLICATIONS

This application claims benefit of Provisional Application No. 60/602,630, filed Aug. 19, 2004, the entire contents of which are hereby incorporated by reference as if fully set forth herein, under 35 U.S.C. §119(e).

STATEMENT OF GOVERNMENTAL INTEREST

This invention was made with Government support under a merit review grant from the U.S. Department of Veterans Affairs and NIH Grant No. DK53732, awarded by the National Institute of Diabetes, Digestive and Kidney Diseases. The Government has certain rights in the invention.

BACKGROUND OF THE INVENTION

1. Field of the Invention

The present invention relates to immunogenic peptides derived from human prostate cancer antigen (PSA-derived peptides) and their use as vaccines to treat or prevent prostate cancer. The invention is also related to dendritic cells from a patient having prostate cancer, which dendritic cells have been exposed to one or more PSA-derived peptides, and their use to treat or prevent prostate cancer in the patient. The invention is also directed to T-cells from a patient which cells are specific for PSA-activated peptide(s), and their uses to treat or prevent prostate cancer.

2. Description of the Related Art

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S. In 1996; 317,000 new cases of prostate adenocarcinoma were diagnosed and over 41,400 men died of the disease (Karp et al., 1996). Only lung cancer has a higher mortality. The chance of a man developing invasive prostate cancer during his lifetime is 1 in 6 or 15.4% at the age of 50; a man has a 42% chance of developing prostate cancer and 2.9% of dying from the disease. While advances in early diagnosis and treatment of locally confined tumors have been achieved, prostate cancer is incurable once it has metastasized. Unfortunately, patients with metastatic prostate cancer on hormonal therapy will eventually develop an androgen-refractory (androgen independent) state that will lead to disease progression and death. In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have thus far shown limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

The PSA blood test has revolutionized the early diagnosis of prostate cancer and the effectiveness of treatment. PSA is a proteolytic enzyme in the family of serine proteases and one of the most abundant proteins in the prostate secretions. Current methods of treatment include radical prostatectomy, radiation, and hormonal suppression. To determine the appropriate method of treatment, factors such as the age of the patient and severity of the disease are often considered. The disease generally is more aggressive for younger patients. Any tumor greater than 0.5 cc is typically considered clinically significant. The preferred treatment for localized prostate cancer is radical prostatectomy. This treatment may result in death, incontinence, impotence, rectal injury, or pulmonary emboli.

In the last 15 years two sentinel insights in the immunotherapy of cancer have become clear; a) patients with cancer do, in fact, have an immune response to their tumor and, b) the target of the immune response in these patients are usually antigens derived from normal self proteins to which the cancer-bearing state has somehow released self tolerance. Hence, cancer reactivity is self reactivity, and the characteristics of a successful cancer immunotherapy will likely resemble autoimmunity. Specific immunotherapy of cancer has therefore consisted, for the most part, of the identification of and vaccination with such antigens by a variety of strategies in the hopes of augmenting the immune response to cancer antigens and bringing about a therapeutic effect. The development of immunotherapy for prostate cancer based on this model is in its infancy compared to other malignancies. Yet, prostate cancer is ideal for this approach because the disease is common, tends to be slowly progressive and any destruction of normal prostate tissue is of no apparent consequence.

Thus, it is desirable to provide improved methods of treatment for prostate cancer that reduce the likelihood of one or more of these unpleasant side effects. In particular, it is desirable to provide improved methods of treatment that reduce the likelihood of the treatment rendering the patient impotent. Finally, no effective treatment currently exists for patients with prostate cancer that has spread outside the prostate gland; these men have the highest risk of death for prostate cancer.

DEFINITIONS

The term "polynucleotide(s)," as used herein, means a single or double-stranded polymer of deoxyribonucleotide bases and includes genomic DNA and recombinant DNA, as well as wholly or partially synthesized polynucleotides.

The term "DNA construct" means a vector having a promoter operably linked to a DNA molecule. The DNA molecule can be a polyepitope DNA molecule, or a multiepitope DNA molecule.

The term "polyepitope" means a single epitope repeatedly expressed in a single peptide, or in a DNA molecule encoding multiple repeats of the single epitope.

The term "multiepitope" means multiple different peptide epitopes in a single peptide or in a DNA molecule encoding the multiple different epitopes.

The term "minigene" means a DNA construct encoding one or more peptides or proteins under the control of one or more promoters.

The term "promoter" means a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate.

The term "operably linked" means a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein-coding regions in the same reading frame.

The term "Prostate-specific antigen-derived MHC Class II-restricted peptides" (hereinafter "PSA-derived peptide") and "HLA-DRB1*1501-restricted T-cell epitope from prostate-specific antigen" mean a peptide having amino acid SEQ ID NOs. 2, 4, 6, 8, 10 or 12, or any portion, fragment, or variant thereof, as well as wholly or partially synthesized peptides.

The term "DNA encoding a PSA-derived peptide" means a DNA polynucleotide having SEQ ID NOs. 1, 3, 5, 7, 9, and 11, or any portion, fragment, or variant thereof, as well as wholly or partially synthesized polynucleotides. It will be appreciated by those of ordinary skill in the art that, as a result of the degeneracy of the genetic code, there are many nucleotide sequences that encode a peptide as described herein. Some of these polynucleotides bear minimal homology to the nucleotide sequence of any native gene. Nonetheless, polynucleotides that vary due to differences in codon usage are specifically contemplated by the present invention.

The term "PSA-derived peptide variants" means polynucleotides that may contain one or more substitutions, additions, deletions and/or insertions such that the therapeutic, antigenic and/or immunogenic properties of the peptides encoded by the variants are not substantially diminished, relative to the corresponding PSA-derived peptide. Such modifications may be readily introduced using standard mutagenesis techniques, such as oligonucleotide directed site-specific mutagenesis as taught, for example, by Adelman et al. (DNA, 2:183, 1983). Preferably, the antigenicity or immunogenicity of a peptide variant is not substantially diminished. Certain variants of the peptides of the present invention are listed in Tables 1-4. Variants also include what are sometimes referred to as "fragments." The term also includes peptides that may contain one or more amino acid substitutions, additions, deletions and/or insertions, some of which as are described herein and in Table 5, such that the therapeutic, antigenic and/or immunogenic properties of the peptide variants are not substantially diminished, relative to the corresponding PSA-derived peptide.

An "isolated" peptide or polynucleotide is one that is removed from its original environment. For example, a naturally-occurring protein is isolated if it is separated from some or all of the coexisting materials in the natural system. Preferably, such peptides are at least about 90% pure, more preferably at least about 95% pure and most preferably at least about 99% pure. A polynucleotide is considered to be isolated if, for example, it is cloned into a vector that is not a part of the natural environment. In general, peptides (including fusion proteins) and polynucleotides as described herein are isolated.

BRIEF DESCRIPTION OF THE DRAWING

The present invention is illustrated by way of example, and not by way of limitation, in the figures of the accompanying drawings and in which like reference numerals refer to similar elements and in which:

FIG. 6 shows responses of human CD4 T-cell lines specific to PSA peptides to natively processed $PSA_{171-190}$ (FIG. 6A) or peptide $PSA_{221-240}$ (FIGS. 6B and 6C) that were incubated with mature autologous DC pulsed with different concentrations of highly purified PSA from human semen. Data are mean±SD of triplicate determinations. The responses for patient Pr116 at the $3^{rd}$ IVS (A) and patient Pr131 at the $4^{th}$ (FIGS. 6B and 6C) or the $5^{th}$ IVS (FIGS. 6B and 6C—insert) are shown. Insert: Cells were cultured in the presence of anti-HLA-A, B, C, anti-HLA-DR antibodies or control IgG2a.

SUMMARY OF THE INVENTION

Figure 1C:
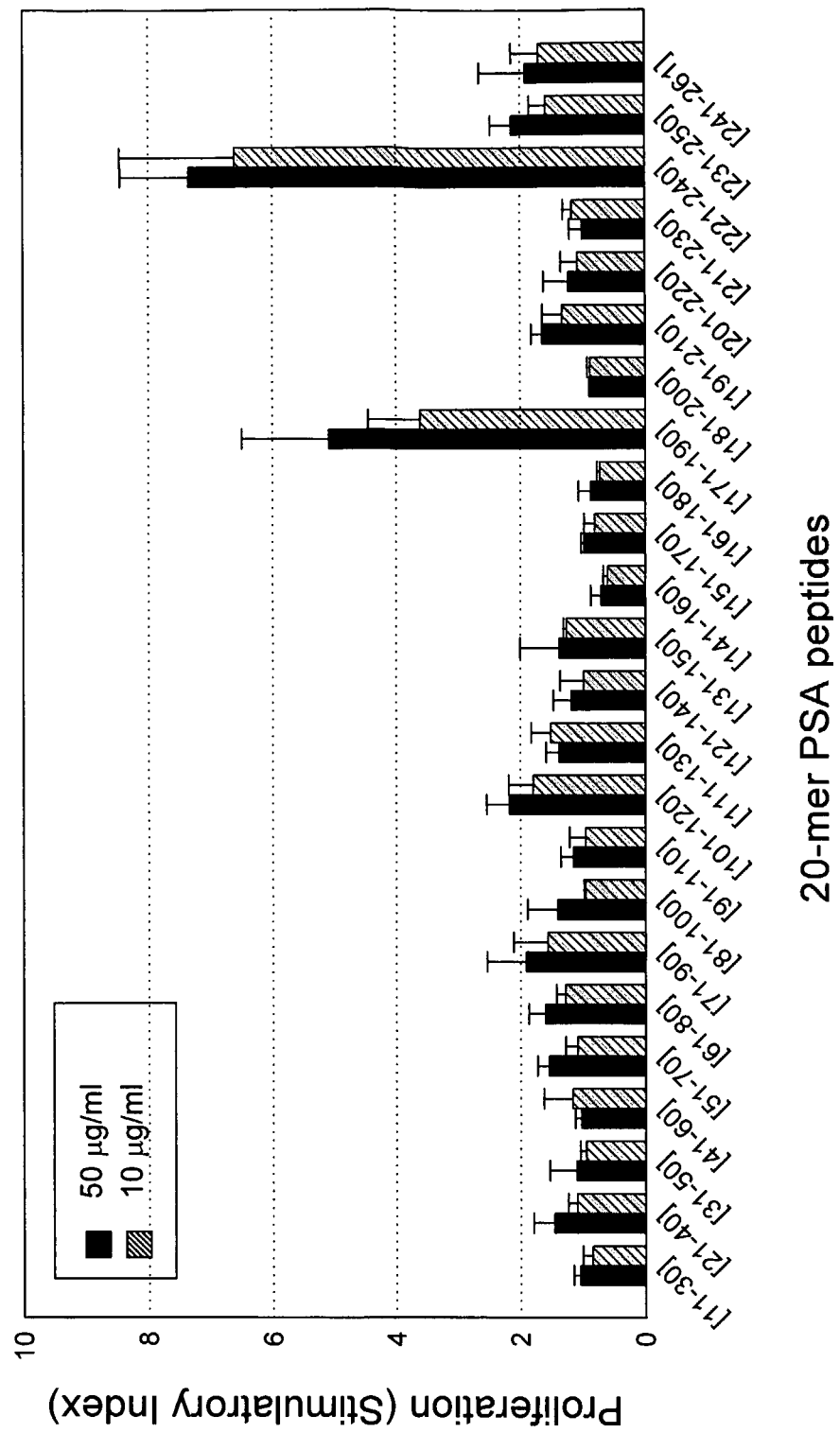
FIG. 1. Recall proliferation assay in draining lymph node cells (DLN) after PSA immunization.
FIG. 1A. Responses to PSA.
FIG. 1B. Sequence of human PSA. C. Proliferation responses to PSA-derived overlapping 20-mer peptides.

Certain aspects of the present invention include PSA-derived peptides and DNA molecules encoding them. For example, an aspect includes an isolated DNA molecule that encodes PSA-derived peptides and has a nucleotide sequence of SEQ ID NOs: 1, 3, 5, 7, 9 or 11; or a variant thereof. Another aspect includes PSA-derived peptides that have amino acid sequences of SEQ ID NOs. 2, 4, 6, 8, 10, and 12; and variants thereof as set forth in Tables 2, 3, 4 and 5. Another aspect includes a DNA construct comprising at least one copy of a first DNA molecule encoding a PSA-derived peptide or variant as just described, operably linked to a promoter that drives expression in a host cell. The DNA construct can have copies of a second DNA molecule encoding a different PSA-derived peptide of the present invention. Other aspects are directed to vaccines for treating or preventing prostate cancer in a male animal that include at least one of the PSA-derived peptides or variants of them.

Another aspect is directed to a fusion protein that includes at least one of the PSA-derived peptides or variants of them, and their use as prostate cancer vaccines. Some further aspects include naked DNA vaccines, or minigene vaccines, that include DNA encoding one or more PSA-derived peptides or variants of them, or fusion proteins as described. A further aspect includes a method of stimulating an immune response to prostate cancer antigens in a male patient by administering to the patient one of the described vaccines.

Another aspect includes dendritic cells isolated from a male patient having prostate cancer or exposed to prostate specific antigen or one of the PSA-peptides of the present invention. An aspect is also directed to vaccines for treating or preventing prostate cancer in a male patient that include these dendritic cells. A further aspect is directed to isolated T-cells from a male patient having prostate cancer or exposed to prostate specific antigen or one of the PSA-peptides of the present invention, and to the use of such T-cells as a vaccine against prostate cancer.

DETAILED DESCRIPTION

The present invention is generally directed to prostate-specific antigen-derived MHC Class II-restricted peptides (hereinafter "PSA-derived peptides") and variants thereof, to the DNA polynucleotides encoding them and variants thereof, and to vaccines for preventing and treating prostate cancer that include these peptides or polynucleotides. In some embodiments, the vaccine includes more than one PSA-derived peptide with a suitable carrier and optionally with non-specific immune response enhancers. In one embodiment the vaccine is a "minigene" of naked DNA encoding one or more copies of the PSA-derived peptides in a suitable expression vector. Other embodiments are directed to fusion proteins that have one or more of the PSA-derived peptides of the present invention, and the DNA polynucleotides encoding them.

Certain embodiments of the present invention are directed to T-cells specific for one or more of the PSA-derived antigens of the present invention. Certain embodiments are further directed to T-cell vaccines and dendritic cell vaccines. Certain further embodiments are directed to methods of treating prostate cancer in a male animal by administering the PSA-derived peptides, or the dendritic cell or T-cell vaccines of the present invention to the patient to increase the immune response to prostate cancer.

Effective vaccination against tumors requires generation of both CD8+ and CD4+ T-cell responses. A critical role of CD4+ helper T-cells in the development of CD8+ tumor-specific effector function has been demonstrated by numerous studies (reviewed in (1)) The role of CD4+ T-cells as effectors mediating autoimmune responses, the immunodominant antigens and their epitopes that can trigger the autoimmune responses (as well as susceptible and resistant MHC haplotypes) has not been sufficiently studied in application to cancer immunotherapy based on self-antigens. This is particularly true for prostate cancer.

CD4 T-cells play an important role in the development of anti-tumor immune responses, yet the identification of naturally processed MHC Class II restricted epitopes derived from prostate differentiation antigens has not been described. In earlier work we studied HLA alleles in GP is a chronic inflammatory condition of the prostate of unknown cause where granulomas and a chronic inflammatory infiltrate can destroy prostatic ducts and glands (8), exactly the responses it is desirous to induce in patients with prostate cancer. In earlier work, we showed that T-lymphocytes from a GP patient had a recall response to secreted prostatic proteins especially whole PSA that normal males do not have. CD4 clones produced from the patient were restricted by HLA DRB1*1501, an allele commonly associated with autoimmune diseases such as multiple sclerosis. 12*? HLA typing of other GP patients revealed a link between GP and the phenotypic expression of HLA-DRB1*1501. Alexander, R. B., et al., J Urology, Vol. 171, 2326-2329, June 2004, the entire contents of which are hereby incorporated by reference as if fully set forth herein, under 35 U.S.C. §119(e). A statistically significant association of GP with the HLA-DRB1*1501 type in Caucasian patients was found: 75% of Caucasian GP patients were of the HLA-DRB1*1501 type. There were an inadequate number of black men in the study to determine if a similar association is present in that group.

Briefly, the results presented below describe the discovery of immunogenic PSA-derived MHC class II-restricted peptides (PSA-derived peptides) for use in prostate cancer treatment and prevention, particularly in vaccines. Mice transgenic for HLA-DRB1*1501 immunized with whole human PSA demonstrated a robust dose-dependent immune response to the antigen. Using a screening a library of overlapping 20-mer peptides that span the entire human PSA sequence, two 20-mer peptides ($PSA_{171-190}$ and $PSA_{221-240}$) were identified that were responsible for this reactivity. Immunization of DR2b (used interchangeably with DRB1*1501 in the literature) transgenic mice with these peptides induced specific immunogenic responses, measured as IFN-gamma secretion, to the peptides themselves as well as to whole PSA. It was discovered that $PSA_{171-190}$ and $PSA_{221-240}$ peptides also stimulated CD4 T-cells from HLA-DRB1*1501+ GP patients who have a pre-existing immune response directed against the prostate gland.

Identification of MHC Class II Restricted PSA Peptides

Among prostate differentiation antigens, the immune response to PSA has been studied most thoroughly to date. Cytotoxic T-Lymphocytes that recognize the predicted HLA-A2—as well as -A1, -A3, and -A24—restricted PSA peptides have been generated from peripheral blood mononuclear lymphocytes (PBMCs) of normal donors and prostate cancer patients in several laboratories (2-6). However, the diversity of Class II alleles that can elicit a response to PSA has not been studied in detail. Corman et al. (3) identified HLA-DR4-binding peptides within the PSA sequence; however, their reactivity with the whole protein was not studied.

The search for MHC class II restricted PSA peptides that could be used as vaccines against prostate cancer was concentrated on the HLA-DRB1*1501 molecule because of the strong linkage of this allele with GP. PSA-reactive HLA-DRB1*1501-restricted CD4 T-cell lines have been established from the peripheral blood of a patient with GP providing evidence for an autoimmune etiology of this disease (9). Further, because PSA-derived HLA-DRB1*1501-restricted epitopes are involved in the autoimmune process in patients with GP, it was decided to develop a vaccine that would induce a destructive immune response directed against prostate cancer in HLA-DRB1*1501 patients.

The association of HLA-DRB1*1501 allele with multiple sclerosis has led to the development of transgenic mice (tg) expressing this molecule for the study of experimental autoimmune encephalomyelitis (10; 11). The mice are termed DR2b in reference to the HLA-DR haplotype which contains the HLA-DRB1*1501 gene. In order to search for HLA-DRB1*1501-restricted immunogenic PSA peptides, DR2b tg mice were immunized with whole, human PSA in complete Freund's adjuvant (CFA). After 9 days, draining lymph nodes (DLN) and spleen were harvested and tested for recall responses to the immunizing antigen. The responses to purified protein derivative of Mycobacterium tuberculosis (an essential component of CFA that is an immunological adjuvant) and ConA served as positive controls. DNA synthesis indicating cell proliferation was determined by [$^3$H] thymidine uptake. The data show a robust dose-dependent immune response to PSA in DLN (FIG. 1A). A similar response in spleen was also documented although it was lower in magnitude (data not shown). To obtain this data DR2b tg mice were vaccinated subcutaneous (s.c.) with PSA (100 µg/mouse) in CFA. Nine days later DLN and spleens were harvested, cultured in vitro in medium containing various additives shown for 48 hr. Cultures were pulsed with [$^3$H] thymidine and CPM determined 18 hr later. Data are mean±SD of triplicate assay conditions. FIG. 1A. DLN were cultured in vitro in the presence of indicated concentrations of human PSA. PPD was added at 25 µg/ml, ConA at 0.5 µg/ml.

To identify the specific PSA epitopes that caused the observed reactivity, DR2b tg mice were immunized s.c. with whole PSA in CFA. Lymphocytes recovered from these immunized animals were stimulated with a PSA peptide library consisting of 20-mer peptides that overlap by 10 amino acids and span the entire PSA amino acid sequence. FIG. 1B shows the amino acid sequence of human PSA. The positions of the first and the last residues for each 20-mer peptide are numerically indicated. Of the 24 peptides tested in this experiment, two 20-mer peptides derived from the PSA sequence stimulated proliferative responses both in DLN (FIG. 1C) and spleen (data not shown). These immunogenic PSA-derived MHC Class II-restricted 20-mer peptides are designated $PSA_{171-190}$ (SEQ ID NO. 2) and $PSA_{221-240}$ (SEQ ID NO. 4). $PSA_{171-190}$ is encoded by DNA having SEQ ID NO. 1 and $PSA_{221-240}$ is encoded by DNA having SEQ ID NO. 3. The numbers indicate numbers for the position of the first and the last residues. Nine-mer core sequences for both of these peptides are indicated in bold type. FIG. 1C shows the proliferation responses to PSA-derived overlapping 20-mer peptides. DLN were cultured in vitro in medium containing a series of overlapping 20-mer peptides derived from the primary amino acid sequence of PSA. Stimulation index is calculated by: $CPM_{peptide}/CPM_{medium}$.

TABLE 1

| PSA-DERIVED PEPTIDE | DNA & AMINO ACSEQ ID NO. SEQUENCES |
|---|---|
| $PSA_{171-190}$ 20-mer | DNA SEQ SEQ ID NO. NO. 1 ctt cag tgt gtg gac ctc cat gtt att tcc aat gac gtg tgt gcg caa gtt cac cct cag First AMINO ACSEQ ID NO. SEQ SEQ ID NO. NO. 2 LQCVDLHVISNDVCAQVHPQ |
| $PSA_{221-240}$ 20-mer | Second DNA SEQ SEQ ID NO. NO. 3 ggt gtg ctt caa ggt atc acg tca tgg ggc agt gaa cca tgt gcc ctg ccc gaa agg cct Second AMINO ACSEQ ID NO. SEQ SEQ ID NO. NO. 4 GVLQGITSWGSEPCALPERP |
| $PSA_{169-181}$ 13-mer | Third DNA SEQ SEQ ID NO. NO. 5 aag aaa ctt cag tgt gtg gac ctc cat gtt att tcc aat Third AMINO ACSEQ ID NO. SEQ SEQ ID NO. NO. 6 KKLQCVDLHVISN |
| $PSA_{221-233}$ 13-mer | Fourth DNA SEQ SEQ ID NO. NO. 7 ggt gtg ctt caa ggt atc acg tca tgg ggc agt gaa cca AMINO ACSEQ ID NO. SEQ SEQ ID NO. NO. 8 GVLQGITSWGSEP |
| $PSA_{171-179}$ 9-mer | Fifth DNA SEQ SEQ ID NO. NO. 9 ctt cag tgt gtg gac ctc cat gtt att AMINO ACSEQ ID NO. SEQ SEQ ID NO. NO. 10 LQCVDLHVI |
| $PSA_{223-231}$ 9-mer | Sixth DNA SEQ SEQ ID NO. NO. 11 ctt caa ggt atc acg tca tgg ggc agt AMINO ACSEQ ID NO. SEQ SEQ ID NO. NO. 12 LQGITSWGS |

Figure 2B:
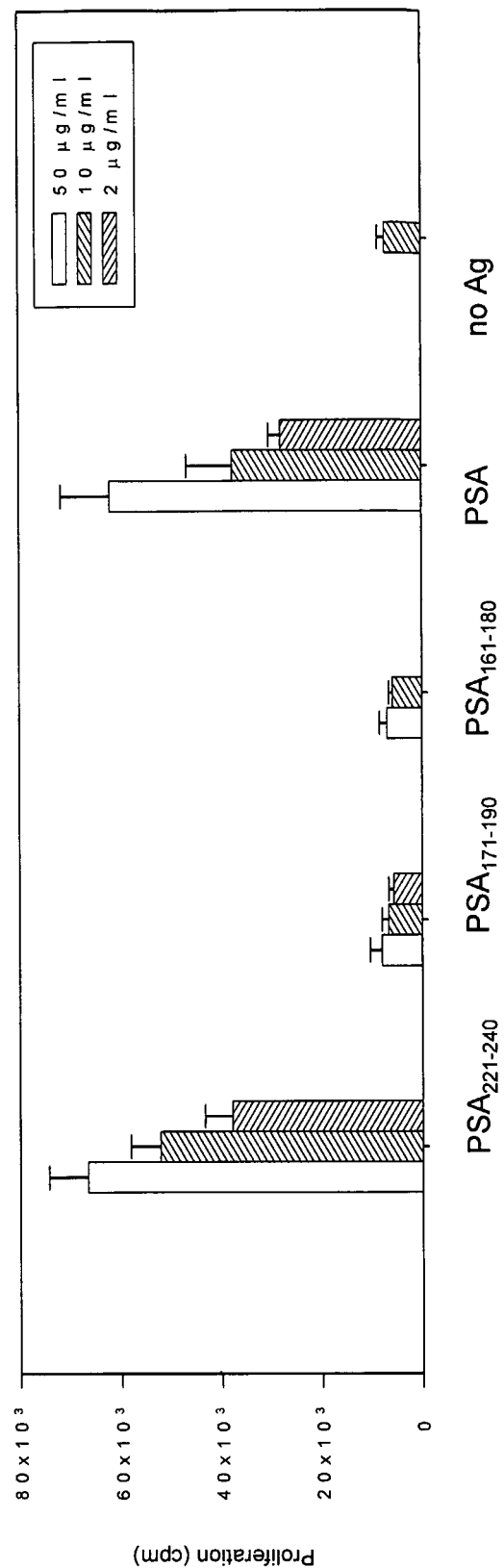
FIG. 2. T-cell proliferation responses induced by immunization with PSA and with peptides $PSA_{171-190}$ (FIG. 2A) or $PSA_{221-240}$ (FIG. 2B).

To confirm the immunogenicity of the two identified 20-mer peptides, DR2b tg mice were immunized s.c. with peptides $PSA_{171-190}$ or $PSA_{221-240}$ in CFA, and DLN cells and splenocytes were harvested 9 days later. DLN T-cells from DR2b Tg mice vaccinated with the peptide $PSA_{171-190}$ showed a moderate proliferation response to $PSA_{171-190}$, and to whole PSA, but only at high antigen concentration (50 µg/ml). (FIG. 2A) Similar data were obtained with splenocytes (data not shown). By contrast, immunization with peptide $PSA_{221-240}$ induced a strong proliferation response at all concentrations (2, 10 and 50 µg/ml) to the peptide $PSA_{221-240}$ itself as well as to whole PSA in DLN (FIG. 2B) and spleen (data not shown). No cross-reaction with peptides $PSA_{161-180}$ or $PSA_{171-190}$ was observed. The responses to the specific peptide were much higher in $PSA_{221-240}$-immunized mice compared to peptide $PSA_{171-190}$-immunized mice, and were seen in a broad range of peptide concentrations.

These data demonstrate that the 20-mer peptides $PSA_{171-190}$ and $PSA_{221-240}$ are naturally processed from whole PSA and they are immunogenic antigens presented by mouse antigen presenting cells (APC) expressing HLA-DRB1*1501. Therefore certain embodiments of the present invention are directed to the PSA-derived peptides $PSA_{171-190}$ and $PSA_{221-240}$ which are encoded by amino acid SEQ ID NOs. 2 and 4, respectively, and to the DNA polynucleotides encoding them having SEQ ID NOs. 1 and 3, respectively.

Development of Human CD4 T-Cell Lines Specific to PSA-Derived 20-mer Peptides $PSA_{171-190}$ and $PSA_{221-240}$ It was next determined whether the PSA epitopes identified in the experiments with transgenic mice can stimulate immune responses in HLA-DR1501+ human males. To accomplish this, short-term CD4 T-cell lines were established from PBMC of several HLA-DRB1*1501+ patients with GP and one patient with prostate cancer (Pr97) by repeated stimulation with either $PSA_{171-190}$ or $PSA_{221-240}$ presented by irradiated autologous PBMC. T-cells were harvested and incubated at 20,000 cells/well with mature autologous dendritic cells (DC) (5,000 cells/well) in the presence or absence of the specific PSA-derived peptide (20 µg/ml). Immunogenicity was measured as IFN-γ secretion in culture supernatants after 48 hr of culture. Data are mean±SD of triplicates. The responses at the $3^{rd}$ IVS (28 days after initiation of culture) are shown.

Figure 3:
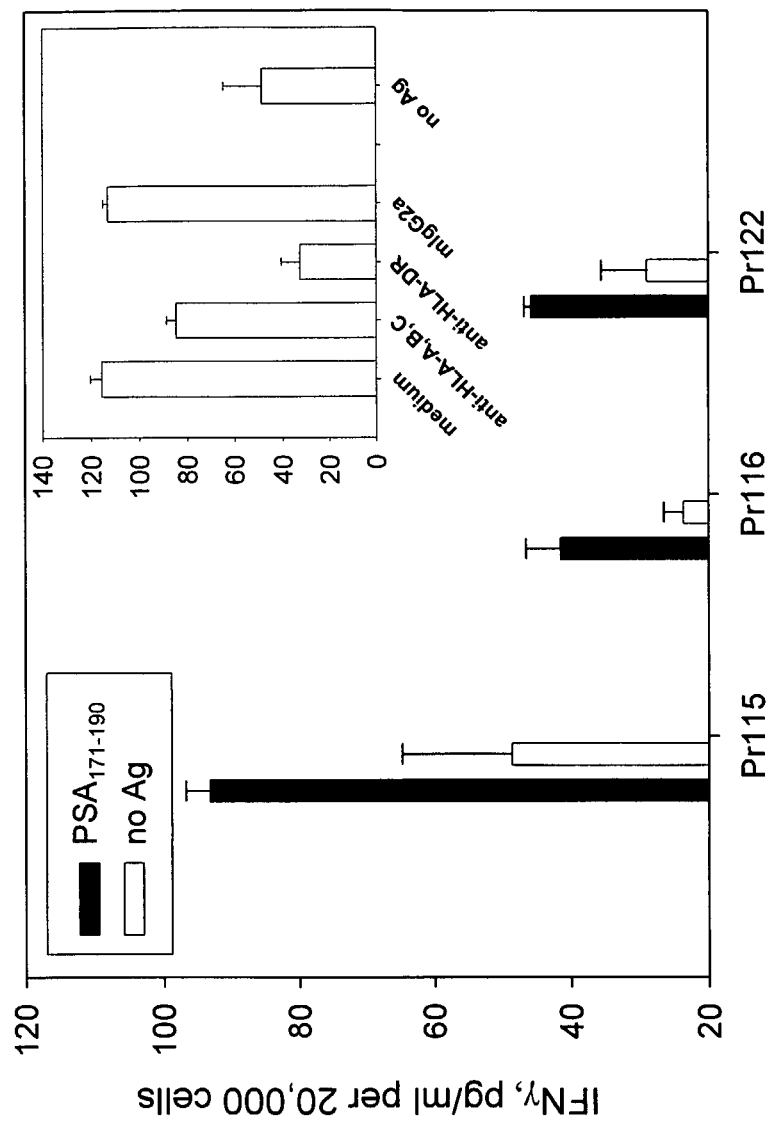
FIG. 3. The responses of human CD4 T-cell lines to peptide $PSA_{171-190}$ presented by autologous DC. Data are mean±SD of triplicates. The responses at $3^{rd}$ in vitro stimulation (IVS) (28 days after initiation of culture) are shown. Insert: T-cells were stimulated in the presence of anti-HLA-A, B, C (clone W6/32), anti-HLA-DR (clone L243) antibodies or control IgG2a (clone IA14) (all mAbs were added at 5 µg/ml).

Cultures were tested for reactivity to the 20-mer antigenic peptides measured by IFNγ secretion using irradiated autologous human PBMC, mature autologous dendritic cells (DC), or BLC-DR2b cells as antigen presenting cells (APC). BLC is an abbreviation for human B-cell lymphoma. Relatively weak reactivity with peptide $PSA_{171-190}$ was observed in three out of five patients with GP after the $2^{nd}$ in vitro stimulation (IVS) (FIGS. 3 and 8A); further expansion of the cultures was unsuccessful. The responses to peptide $PSA_{171-190}$ were HLA-DR-restricted since IFN-γ secretion was blocked by the addition of anti-HLA-DR but not anti-HLA-A, B, C mAb (FIG. 3, insert). T-cells were stimulated in the presence of anti-HLA-A, B, C (clone W6/32), anti-HLA-DR (clone L243) antibodies or control IgG2a (clone IA14) (all mAbs were added at 5 µg/ml).

Figure 4A:
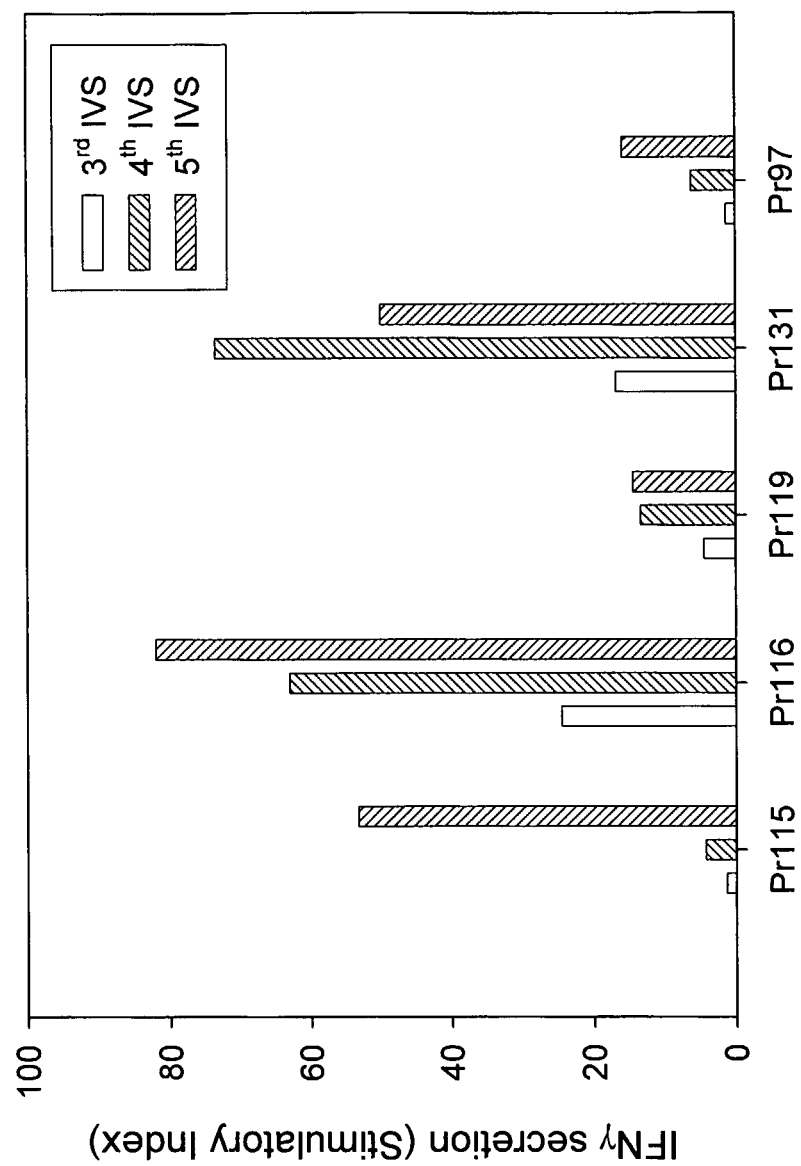
FIG. 4. The responses of human CD4 T-cell lines to peptide $PSA_{221-240}$ presented by BCL-DR2b cell line FIG. 4 A. T-cells were tested at the $3^{rd}$, $4^{th}$ and $5^{th}$ IVS (28, 42 and 56 days after initiation of culture); stimulatory index is calculated by: $Response_{peptide}/Response_{medium}$.
FIG. 4B. The responses at the $4^{th}$ IVS are shown.
Figure 4B:
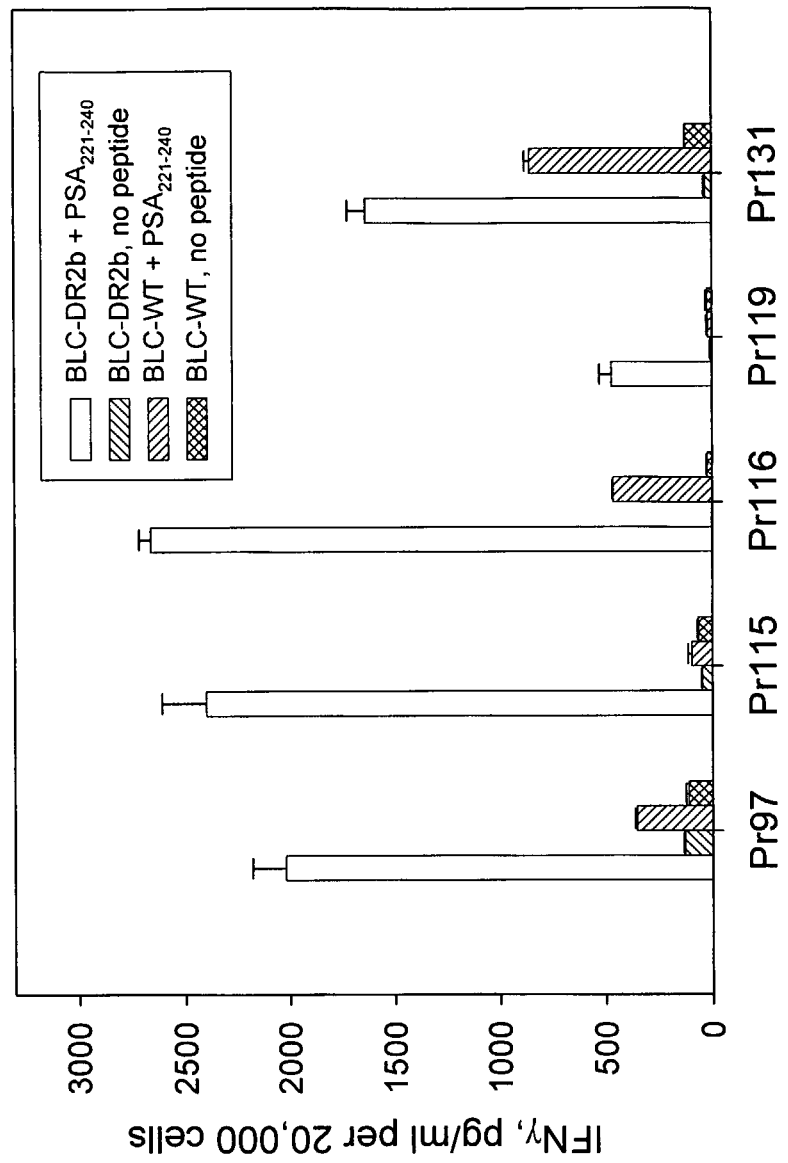

The responses of human CD4 T-cell lines to peptide $PSA_{221-240}$ presented by the BCL-DR2b cell line are shown in FIG. 4. CD4 T-cell lines were generated from 5 different patients by multiple stimulations with peptide $PSA_{221-240}$ in the presence of irradiated autologous PBMC. T-cells were harvested and incubated at 20,000 cells/well with BLC-DR2b or parental BLC cell lines (10,000 cells/well, irradiated at 10,000 rad) in the presence or absence of peptide $PSA_{221-240}$ (20 µg/ml). IFNγ secretion was measured in culture supernatants after 48 hr of incubation. FIG. 3A. T-cells were tested at the $3^{rd}$, $4^{th}$ and $5^{th}$ IVS (28, 42 and 56 days after initiation of culture). The stimulatory index is calculated by: $Response_{peptide}/Response_{medium}$. FIG. 3B. The responses at the $4^{th}$ IVS are shown.

When peptide $PSA_{221-240}$ was used for stimulation, long-term CD4 T-cell lines from all 5 patients were established that showed peptide-specific reactivity at the $3^{rd}$, $4^{th}$ and $5^{th}$ IVS (FIG. 4A). To prove that the responses are HLA-DRB1*1501-restricted, a BLC cell line engineered to express the HLA-DRB1*1501 molecule was used as the APC. It is noted that "HLA-DRB1*1501" and "DR2b" are used interchangeable in the literature. CD4 T-cell lines from all 5 patients demonstrated strong specific responses to the peptide $PSA_{221-240}$ presented by BCL-DR2b cells as measured by IFNγ secretion (FIGS. 4A, B). No responses to $PSA_{221-240}$ presented by parental HLA-DRB1*1501-negative BCL cells were seen in patients Pr115 and Pr119. By contrast T-cell lines from 3 other patients (Pr97, Pr116 and Pr131) showed low levels of reactivity with $PSA_{221-240}$ in HLA-DR2b-independent fashion (FIG. 4A). The parental BCL line expressed HLA-DRB1*03, -DRB1*11, DRB3*01 and DQB1*05 alleles as shown by intermediate resolution PCR-based typing.

Figure 5A:
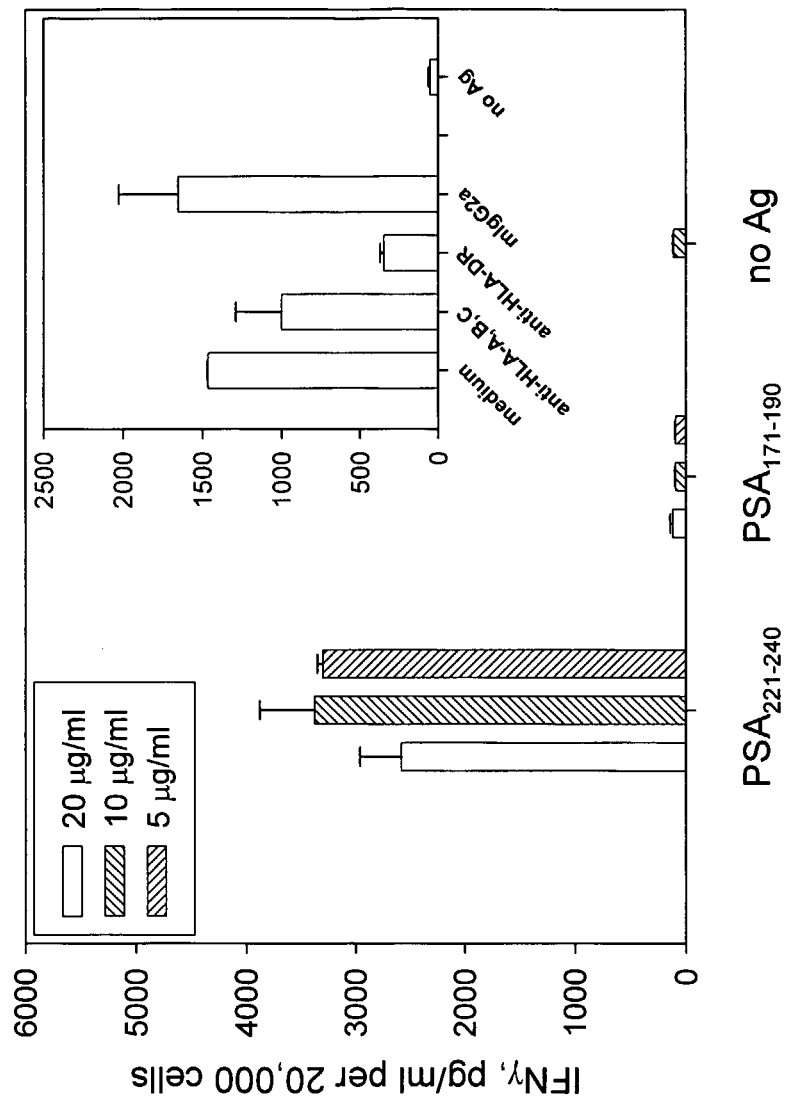
FIG. 5. The responses of human CD4 T-cell lines to peptide $PSA_{221-240}$ presented by autologous dendritic cells. IFNγ secretion was measured in culture supernatants after 48 hr of culture (FIG. 5A). Cultures were then pulsed with [$^3$H] thymidine and CPM determined 18 hr later (FIG. 5B). Data are mean±SD of triplicate determinations. The response for patient Pr131 at the $4^{th}$ IVS is shown. Insert: Cells were cultured in the presence of anti-HLA-A, B, C, anti-HLA-DR antibodies or control IgG2a. The response for patient Pr131 at the $5^{th}$ IVS is shown.
Figure 5B:
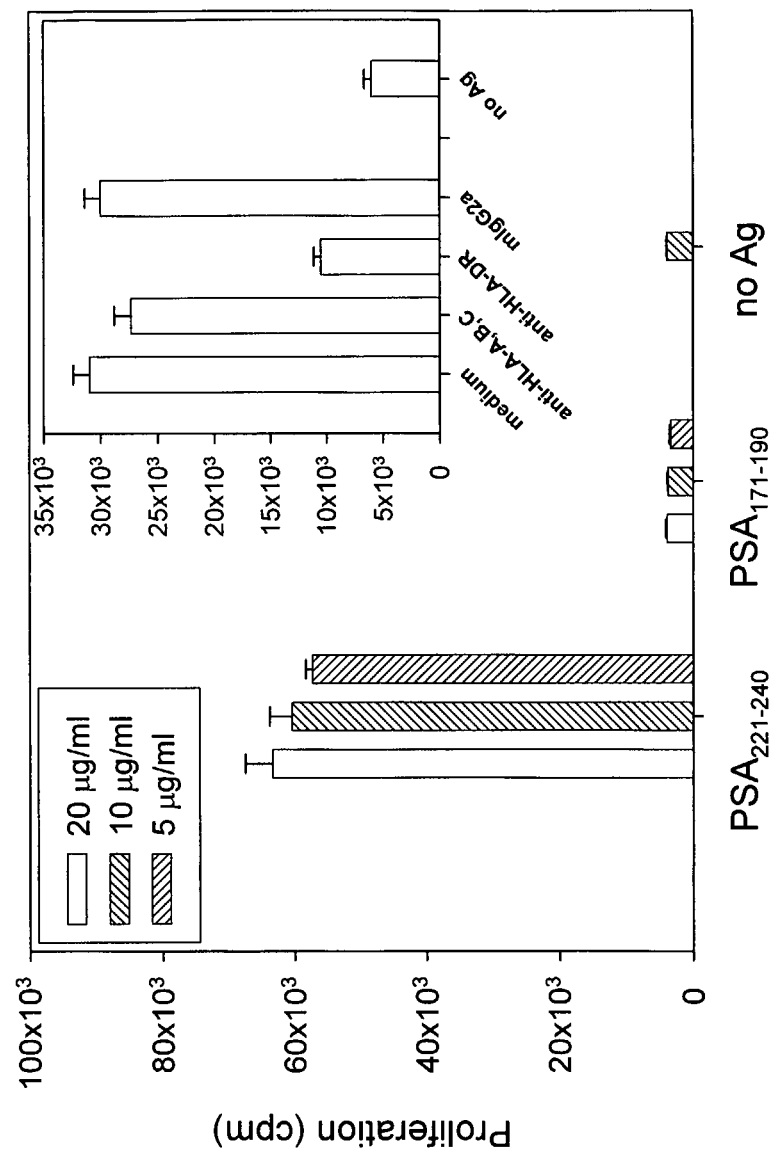

FIG. 5 shows the responses of human CD4 T-cell lines to peptide $PSA_{221-240}$ presented by autologous dendritic cells. CD4 T-cells specific to peptide $PSA_{221-240}$ were incubated with mature autologous DC (5,000 cells/well) and $PSA_{221-240}$ peptides at different concentrations. IFNγ secretion was measured in culture supernatants after 48 hr of culture (FIG. 5A). Cultures were then pulsed with [$^3$H] thymidine and CPM determined 18 hr later (FIG. 5B). Data are mean±SD of triplicate determinations. The response for patient Pr131 at the $4^{th}$ IVS is shown. FIG. 5 insert shows cells cultured in the presence of anti-HLA-A, B, C, anti-HLA-DR antibodies or control IgG2a. The response for patient Pr131 at the $5^{th}$ IVS is shown. Proliferation and IFN-γ secretion were seen in a broad range of peptide concentrations (from 40 µg/ml to 5 µg/ml) as shown in representative experiments for patient Pr131 (FIGS. 5A and 5B) and patient Pr97 (FIGS. 8B, and 8C). No cross-reactivity with peptide $PSA_{171-190}$ was observed. The HLA-Class II restriction of $PSA_{221-240}$-specific T-cell lines was confirmed using blocking mAbs to HLA-DR (FIGS. 5A, 5B, and 5 insert). The phenotype of all T-cell lines was exclusively CD4-positive and CD8 negative as determined by immunofluorescence staining at the $3^{rd}$ IVS (data not shown). The analyses of sequence similarity of both epitopes to the human proteome were conducted using the PIR non-redundant reference protein database and peptide match program (17). For any 5-mer motifs within the 20-mer amino acid sequences, PSA 171-190 demonstrated a maximum of 4 matches, and $PSA_{221-240}$ a maximum of 7 matches (data not shown). This suggests that the new PSA-derived epitopes are likely to be effective antigens for use in vaccines.

Peptides bind to HLA class I and class II complexes on the surface of antigen presenting cells and are presented to CD4 and CD8 T lymphocytes. The peptide-HLA complex is the antigen to which the T cell receptor binds and signals the lymphocyte to move into the activated state. The binding of peptides to HLA is determined by the sequence of the peptide with certain amino acid residues having critical roles (anchor residues) in binding the peptide to the binding groove of the HLA complex. Class I peptide motifs for each class I HLA haplotype are strict and binding of the typical 8-9mer peptides is relatively specific for a given HLA haplotype. However, it is clear that peptides binding to HLA class II are more promiscuous and tend to bind to many different class II haplotypes (1; 2). It is therefore expected that $PSA_{171-190}$ and $PSA_{221-240}$ will bind HLA-DR haplotypes other than HLA-DRB1*1501 or 1503 and can be used as vaccines in a broad range of patients. Preliminary evidence shows that $PSA_{221-240}$ can also be presented by at least HLA-DRB1*03.

Peptide-Specific Human T-Cell Lines Recognize Whole PSA

Figure 6A:
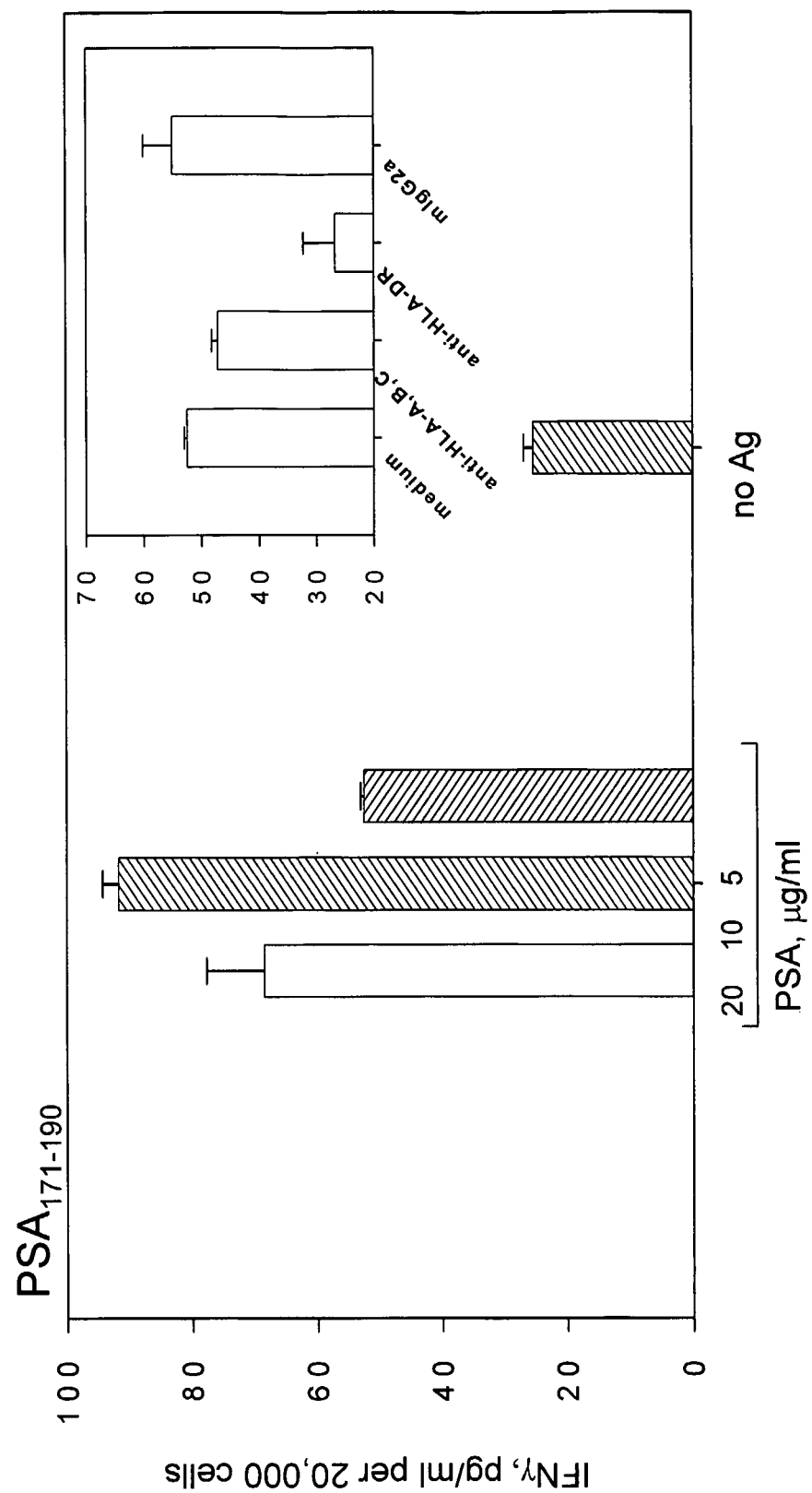
Figure 6B:
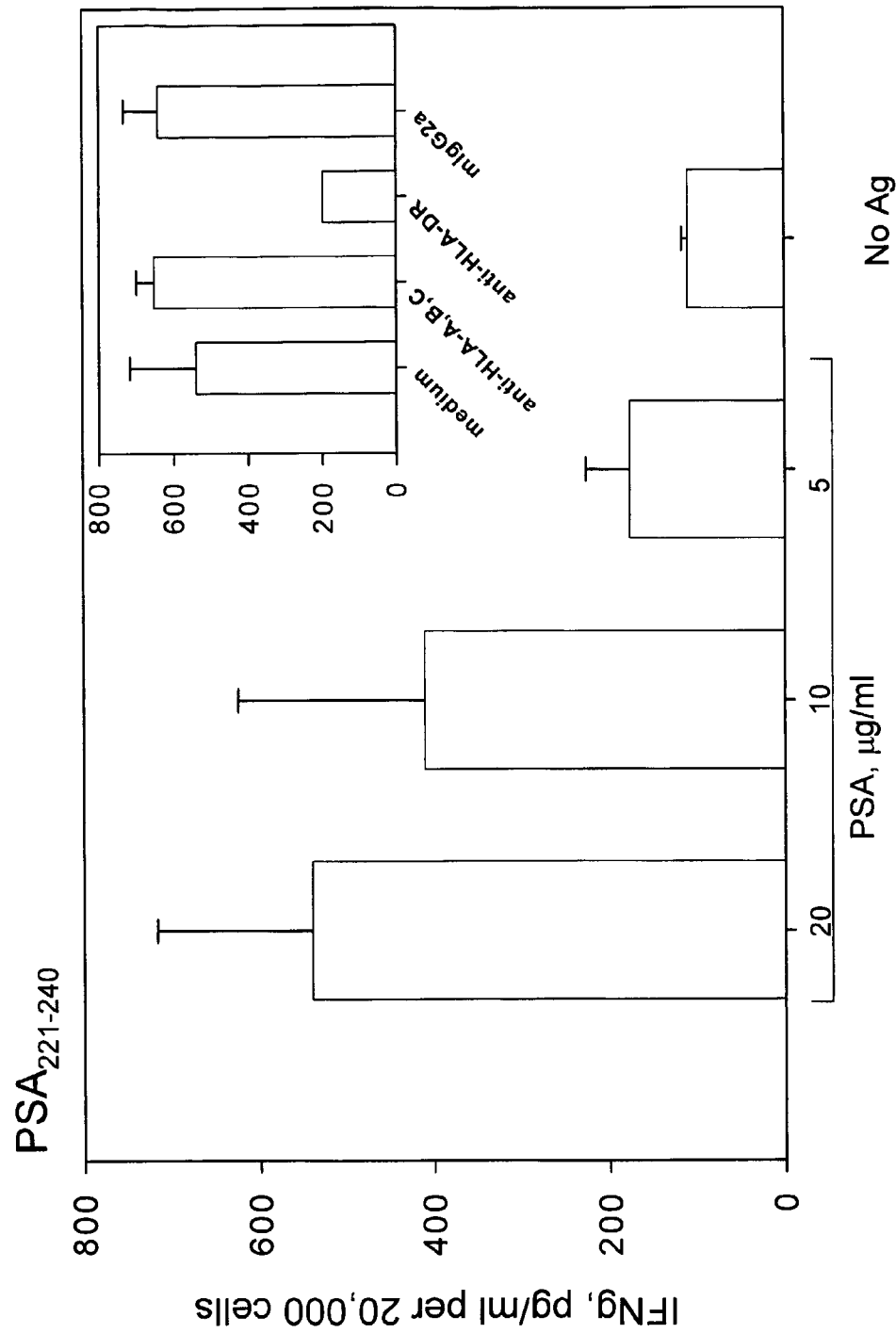
Figure 6C:
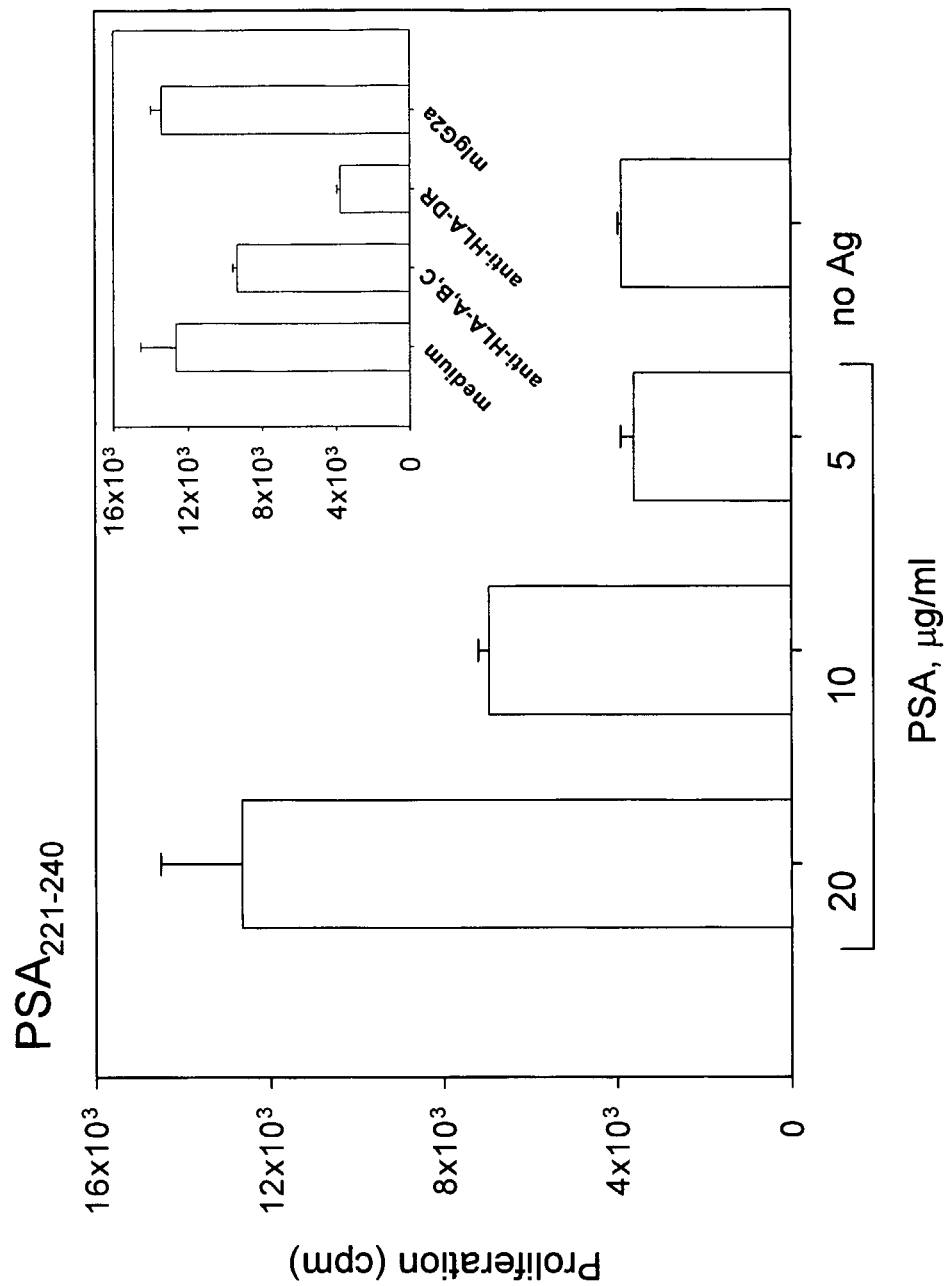

The ability of the peptide-specific T-cell lines to recognize and respond to whole PSA that has been naturally processed was determined next. Since immature rather than mature DCs are known to be the most effective in endocytosing and processing whole proteins, highly purified PSA from human semen was added at various concentrations (as indicated in FIG. 6) to immature autologous DC cultures on day 4 after initiation of DC culture. After 6-8 hr of incubation, rhTNFα and rhIFNα were added for an additional 3 days to induce maturation. FIG. 6A shows CD4 T-cells specific to peptide $PSA_{171-190}$, FIG. 6B shows CD4-T cells specific for peptide $PSA_{221-240}$. IFNγ secretion was measured in culture supernatants after 48 hr (FIGS. 6A and 6B). Cultures were then pulsed with [$^3$H] thymidine and CPM determined 18 hr later (C, D). Data are mean±SD of triplicate determinations. The responses for patient Pr116 at the $3^{rd}$ IVS (A) and patient Pr131 at the $4^{th}$ (B,C) or the $5^{th}$ IVS (B,C-insert) are shown. FIG. 6 insert shows cells cultured in the presence of anti-HLA-A, B, C, anti-HLA-DR antibodies or control IgG2 as described for FIG. 3. Cells stimulated in vitro with peptide $PSA_{171-190}$ produced IFNγ in response to DC pulsed with whole PSA. This shows that the DC processed whole PSA into $PSA_{171-190}$ that was recognized by the CD4 T-cells. The responses were selectively blocked by anti-HLA-DR mAb, but not by HLA-A, B, C-specific mAbs (FIG. 6A, insert). Similar data were obtained with CD4 T-cells from GP patients Pr115 and Pr122 (data not shown). Next it was shown that cultured CD4 T-cell lines stimulated in vitro with peptide $PSA_{221-240}$ similarly secreted IFN-γ (FIG. 6B) and proliferated (FIG. 6C) in response to DC pulsed with whole protein. Again, this shows that the DC processed whole PSA into immunogenic $PSA_{221-240}$.

Figure 7:
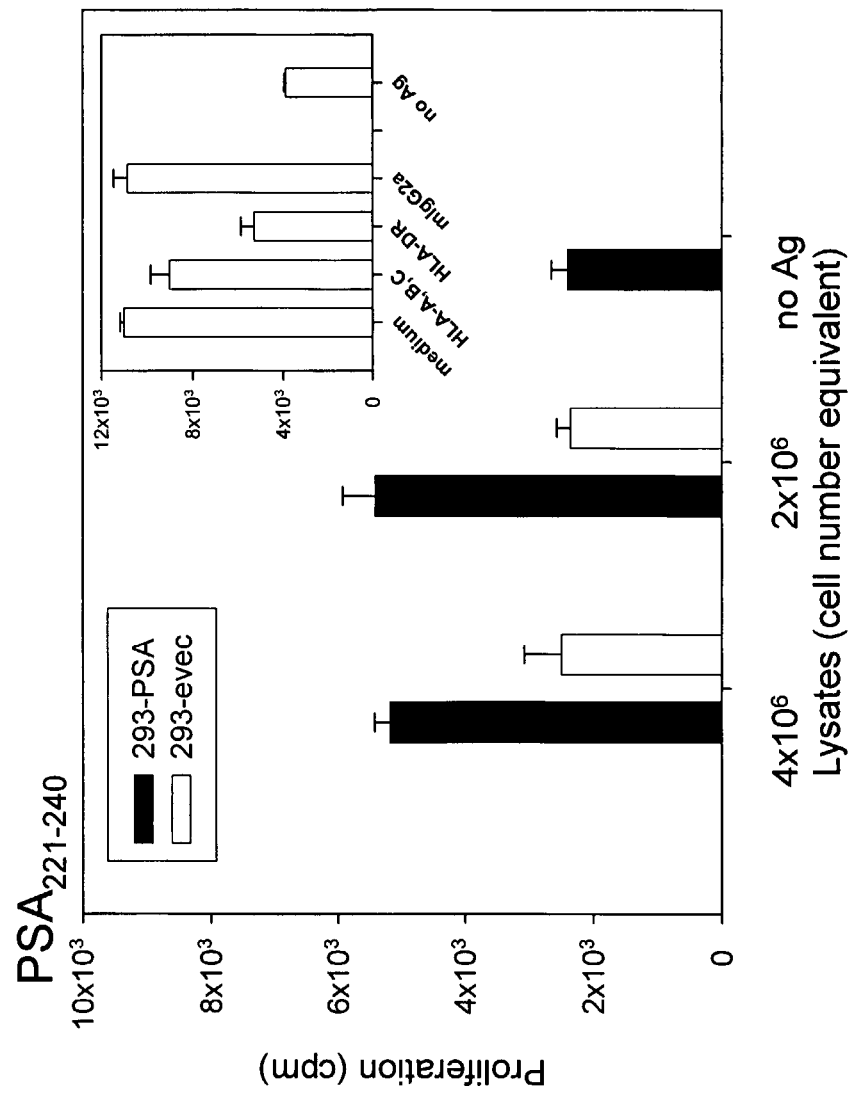
FIG. 7 shows responses of human CD4 T-cell lines specific to peptide $PSA_{221-240}$ to antigen endogenously expressed in tumor cells. Peptide-specific T-cells were incubated with mature autologous DC pulsed with different concentrations of lysate prepared from HEK 293 cell line transfected with PSA (293-PSA) or control "empty" vector (293-evec). After 48 hr of incubation, cultures were pulsed with [$^3$H] thymidine and CPM determined 18 hr later. Data are mean±SD of triplicate determinations. The response for patient Pr131 at the $4^{th}$ IVS is shown. Insert: Cells were cultured in the presence of anti-HLA-A, B, C, anti-HLA-DR antibodies or control IgG2a as described in the legend to FIG. 3. The response for patient Pr131 at the $5^{th}$ IVS is shown.

Another series of experiments was conducted to ensure that T-cells specific for peptide $PSA_{221-240}$ can recognize PSA endogenously expressed in tumor cells. FIG. 7 shows responses of human CD4 T-cell lines specific for peptide $PSA_{221-240}$ to antigen endogenously expressed in tumor cells. Peptide-specific T-cells were incubated with mature autologous DC pulsed with different concentrations of lysate prepared from the HEK 293 cell line transfected with PSA (293-PSA) or control "empty" vector (293-evec). After 48 hr of incubation, cultures were pulsed with [$^3$H] thymidine and CPM was determined 18 hr later. Data are mean±SD of triplicate determinations. The response for patient Pr131 at the $4^{th}$ IVS is shown. FIG. 7 insert shows cells that were cultured in the presence of anti-HLA-A, B, C, anti-HLA-DR antibodies or control IgG2a as described in the legend to FIG. 3. The response for patient Pr131 at the $5^{th}$ IVS is shown in FIG. 7. $PSA_{221-240}$-specific T-cells from patient Pr131 responded to DC pulsed with PSA-containing cell lysate, but not with control lysate. The responses to the 293/PSA lysate were blocked with HLA-DR mAb showing that the responses were HLA-DR-restricted (FIG. 7, insert). Similar results were obtained for other GP patients (Pr115, Pr116 and Pr119) and prostate cancer patient Pr97 (data not shown).

These experiments demonstrate that the newly identified peptides $PSA_{171-190}$ and $PSA_{221-240}$ are capable of stimulating human T-cells and these T-cells are capable of recognizing naturally processed and presented PSA peptides. Thus another embodiment of the present invention is directed to vaccines for treating or preventing prostate cancer in a male animal that include one or both of the newly discovered PSA-derived immunogenic peptides $PSA_{171-190}$ and $PSA_{221-240}$ and fragments of variants thereof. The vaccines of the present invention can optionally have non-specific immune response enhancers including interleukins like IL-12 (IL12), granulocytes-macrophage colony-stimulating factor (GM-CSF), chemokines and defensins including β2-defensin, β-3 defensin, MIP3α or other adjuvant molecules such as fragment C (FrC) of tetanus toxin or heat shock protein 70-like protein 1 (Hsp70L1). Other immune response enhancers include dendritic cells, cytokines, chemokines, KLH, bacterial organisms or parts thereof (like BCT), killed bacteria, and others known in the art. The preferred adjuvant for use in the prostate cancer vaccines of the present invention is incomplete Freund's adjuvant (CFA), also known as Mountamide ISA51, made by Seppic, a Canadian company. Any adjuvant approved for human use can be included in the vaccines of the present invention. More discussion of the formulation and administration of vaccines is presented below.

Genetic Minigene Vaccines

Genetic prostate cancer vaccines made of naked DNA minigenes also come within the scope of the present invention. Thus another embodiment of the invention is a prostate cancer vaccine made of naked DNA minigenes encoding PSA-derived antigens, including $PSA_{171-190}$ or $PSA_{221-240}$ or combinations thereof, or their respective variants. The naked DNA vaccines can be polyepitopes, or multiple epitopes of the $PSA_{171-190}$ or $PSA_{221-240}$ polynucleotides. The peptide epitope sequences can be expressed as single epitope or as linked epitopes in a string of beads configuration, such that a single peptide is produced containing multiple copies of a single epitope, or single or multiple copies of multiple epitopes. Tine, J. A., et al, Enhanced multiepitope-based vaccines elicit CD8+ cytotoxic T cells against both immun- odominant and cryptic epitopes, Elsevier Ltd., 2004, Vaccine 23 (2005)1085-91, the entire contents of which are hereby incorporated by reference as if fully set forth herein, under 35 U.S.C. §119(e). The epitopes could be assembled into either single peptide chain or expressed under separate promoters. For example, poxvirus such as attenuated poxvirus canarypox (ALVAC) vectors are excellent vehicles for the insertion of multiple genes, each on its own promoter because they can accept large amounts of DNA and numerous poxvirus promoters are known. Tsang, K. Y., et al., Analyses of Recombinant Vaccinia and Fowlpox Vaccine Vectors Expressing Transgenes for Two Human Tumor Antigens and Three Human Costimulatory Molecules, Clinical Cancer Res. Vol. 11, 1597-1607, Feb. 15, 2005, and Tine, ID., the entire contents of which are hereby incorporated by reference as if fully set forth herein, under 35 U.S.C. §119(e). This approach is widely used in the development of vaccines against cancer. Virtually all tumors express multiple tumor-associated antigens and most of them are heterogeneously expressed in tumor masses so vaccines expressing multiple epitopes may well exploit antigenic heterogeneity.

Determination of the Minimal Epitope.

The amino acid sequences for the peptides $PSA_{171-190}$ and $PSA_{221-240}$ were analyzed using the ProPred computer algorithm (18). The analysis indicated that both 20-mers contain 9 amino-acid HLA-DR1501-binding predicted core motifs, $PSA_{171-179}$ and $PSA_{223-231}$ with a score of 2.9 (30% of maximal achievable score) for both sequences. No immunogenic responses were observed with the 9-mer core sequences for the HLA-DRB1*1501-binding epitopes $PSA_{171-179}$ and $PSA_{223-231}$, or with adjacent overlapping 20-mer peptides. Therefore, 13-mer peptides $PSA_{169-181}$ and $PSA_{221-233}$ were designed by adding 2 flanking amino acids to both sides of the core peptide (FIG. 1B). Other embodiments of the invention therefore include the peptides $PSA_{171-179}$ (SEQ ID NO. 10), $PSA_{223-231}$ (SEQ ID NO. 12), $PSA_{169-181}$ (SEQ ID NO. 6) and $PSA_{221-233}$ (SEQ ID NO.8); the DNA polynucleotides encoding them $PSA_{171-179}$ (SEQ ID NO. 9), $PSA_{223-231}$ (SEQ ID NO. 11), $PSA_{169-181}$ (SEQ ID NO. 5) and $PSA_{221-233}$ (SEQ ID NO. 7); and vaccines that include one or more of these peptides, including minigene vaccines as described above. See also Table 1.

Figure 8A:
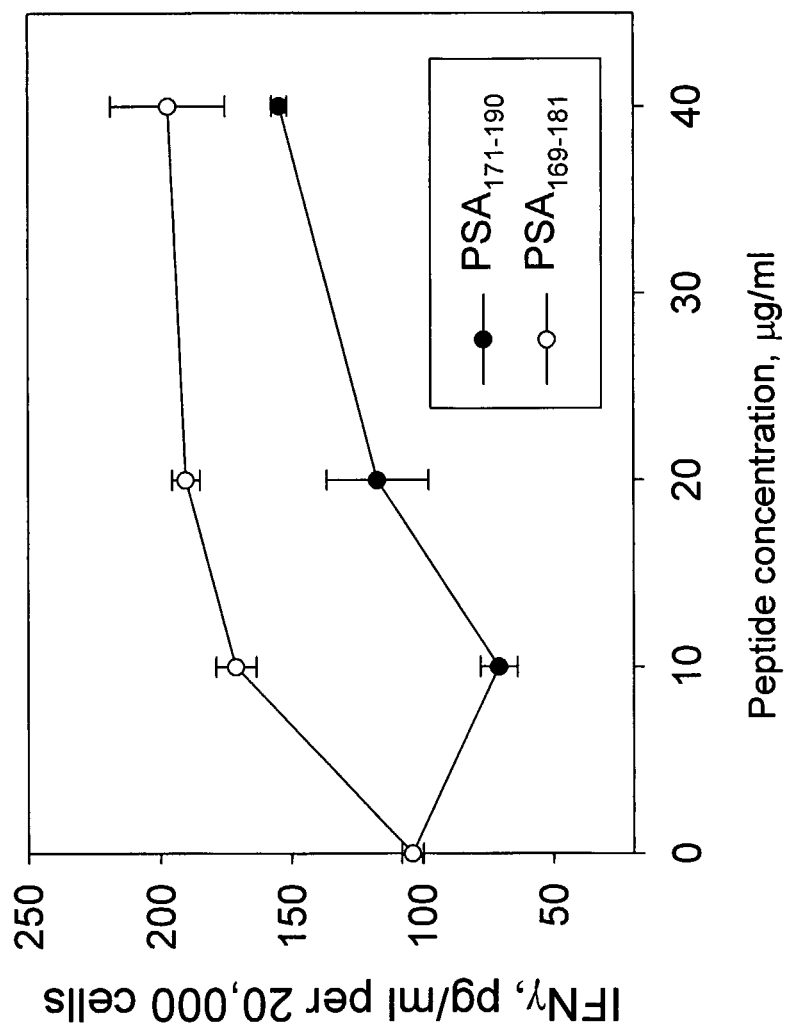
FIG. 8 shows the responses of human CD4 T-cell lines specific to 20-mer peptide $PSA_{171-190}$ (FIG. 8A) and $PSA_{221-240}$ (FIG. 8B and FIG. 8C) to the minimal T-cell determinant. Data are mean±SD of triplicate determinations. The responses for patient Pr115 at the $3^{rd}$ VS (FIG. 8A) and patient Pr97 at the $5^{th}$ IVS (FIG. 8B and FIG. 8 C) are shown.
Figure 8B:
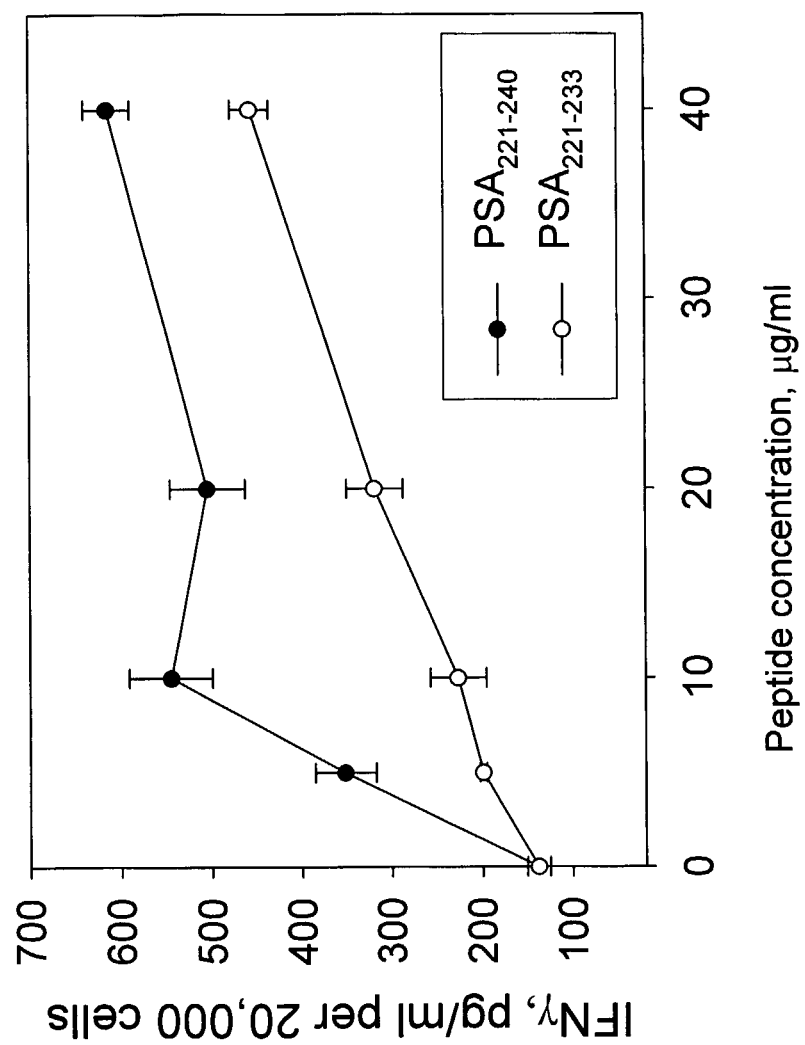
Figure 8C:
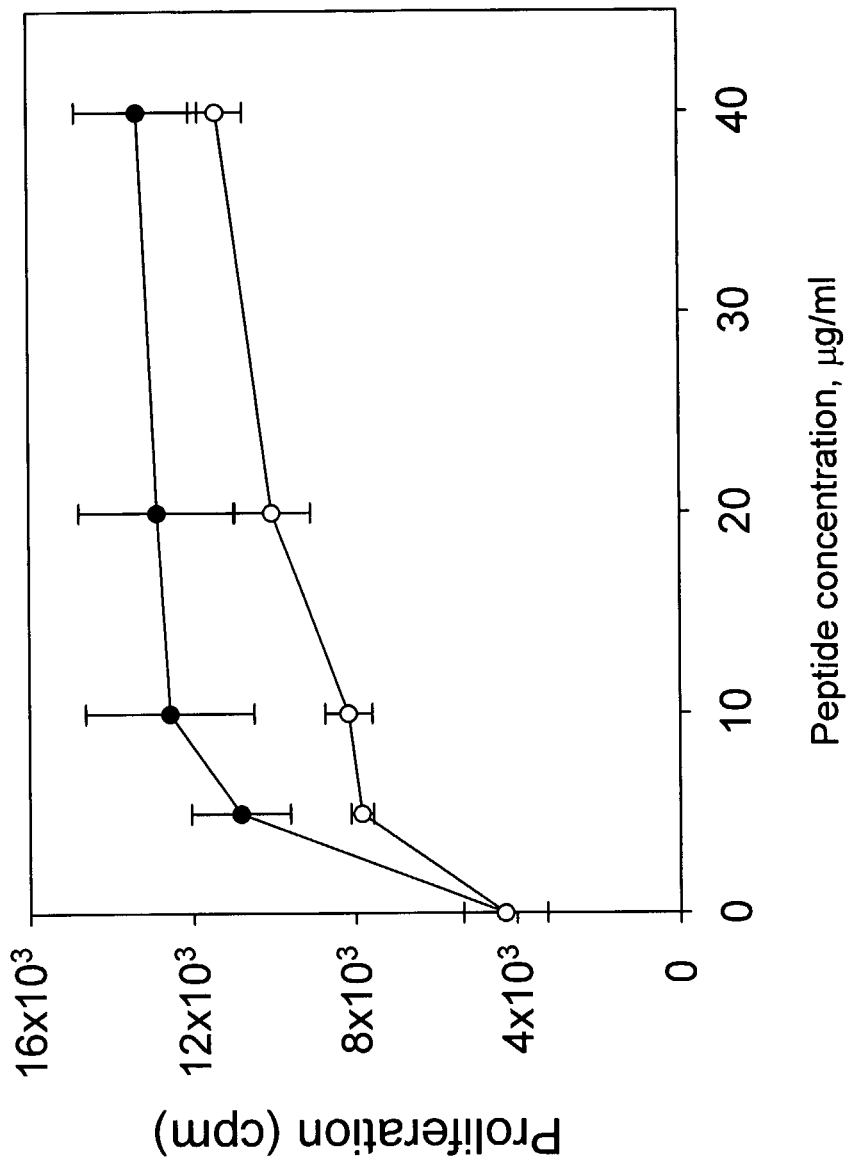

FIG. 8 shows the responses of human CD4 T-cell lines specific for 20-mer peptides $PSA_{171-190}$ and $PSA_{221-240}$ to the minimal T-cell determinant. CD4 T-cell lines specific to $PSA_{171-190}$ (FIG. 8A) or $PSA_{221-240}$ (FIGS. 8B and 8C) were incubated with irradiated autologous PBMC in the presence of different concentrations of original 20-mer peptide (dark circles) or corresponding 13-mer peptide containing core HLA-DRB1*1501-binding epitope (open circles). IFNγ secretion was measured in culture supernatants after 48 hr of culture (FIGS. 8A and 8B). Cultures were then pulsed with [$^3$H] thymidine and CPM determined 18 hr later (FIG. 8C). Data are mean±SD of triplicate determinations. The responses for patient Pr115 at the $3^{rd}$ IVS (A) and patient Pr97 at the $5^{th}$ IVS (FIGS. B, C) are shown.

CD4 T-cell lines specific to either 20-mer peptide $PSA_{171-190}$ (FIG. 8A, patient Pr115) or peptide $PSA_{221-240}$ (FIG. 8B, C, patient Pr97) responded to the corresponding 13-mer peptides. This shows that the minimal T-cell determinants presented by the HLA-DR1501 molecule are present within these sequences. Some embodiments of the vaccines have one or more of the 13 mer peptides or variants thereof, with one or more of the 20-mer peptides described above, or variants thereof. Such vaccines optionally include immune response enhancers as noted herein.

Adoptive Immunotherapy

Immunogenic PSA-derived peptides disclosed herein may also be employed in adoptive immunotherapy for the treatment of cancer. Immunotherapy treatment relies on the in vivo stimulation of the endogenous host immune system to react against tumors with the administration of immune response-modifying agents (for example, tumor vaccines, bacterial adjuvants, and/or cytokines). The vaccines of the present invention come under this category.

In adoptive immunotherapy, treatment involves the delivery of cells with established tumor-immune reactivity that can directly or indirectly mediate antitumor effects and does not necessarily depend on an intact host immune system. Examples of effector cells include T lymphocytes (for example, CD8+ cytotoxic T-lymphocyte, CD4+ T-helper, gamma/delta T lymphocytes, tumor-infiltrating lymphocytes), killer cells, lymphokine-activated killer cells B-cells, or antigen presenting cells (such as dendritic cells and macrophages) expressing the disclosed antigens.

The predominant method of procuring adequate numbers of T-cells for adoptive immunotherapy is to grow immune T-cells in vitro. In certain embodiments of the present invention T-cells or dendritic cells, fibroblasts, B-cells, monocytes or macrophages from the patient are isolated and cultured for future use in prostate cancer therapy as immune system stimulants or vaccines. Dendritic cells, for example, are typically created in vitro from peripheral blood cells. Purified dendritic cells are then stimulated with particular cytokines to cause them to develop. They are then pulsed with PSA-derived antigens that bind to the surface of the dendritic cells. In one embodiment of the present invention, the antigen-primed dendritic cells are then injected into the patient as a dendritic cell vaccine.

Culture conditions for expanding single antigen-specific T-cells to several billion in number with retention of antigen recognition in vivo are well known in the art. These in vitro culture conditions typically utilize intermittent stimulation with immunogenic PSA-derived peptide antigen, often in the presence of cytokines, such as IL-2, and non-dividing feeder cells. As noted above, the immunoreactive peptides described herein may be used to rapidly expand antigen-specific T-cell cultures in order to generate sufficient number of cells for immunotherapy. In particular, antigen-presenting cells, such as dendritic, macrophage, monocyte, fibroblast, or B-cells, may also be pulsed with immunoreactive PSA-derived peptides, or polynucleotide sequence(s) may be introduced into antigen presenting cells, using a variety of standard techniques well known in the art. For example, antigen presenting cells may be transfected or transducers with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T-cells: Principles Revisited," Immunological Reviews, 157:177, 1997) the entire contents of which are hereby incorporated by reference as if fully set forth herein, under 35 U.S.C. §119(e).

In one embodiment the PSA-derived peptides disclosed herein are employed to generate and/or isolate tumor-reactive T-cells, which can then be administered to the patient. In one technique, antigen-specific T-cell lines are generated by in vivo immunization with short peptides corresponding to immunogenic portions of the disclosed peptides. The resulting antigen specific CD8+ CTL clones may be isolated from the patient, expanded using standard tissue culture techniques, and returned to the patient. In this approach, vaccination is combined with adoptive immunotherapy.

Alternatively, peptides corresponding to immunogenic portions of the peptides may be employed to generate tumor reactive T-cell subsets by selective in vitro stimulation and expansion of autologous T-cells to provide antigen-specific T-cells which may be subsequently transferred to the patient as described, for example, by Chang et al, (Crit. Rev. Oncol. Hematol., 22(3), 213, 1996), the entire contents of which are hereby incorporated by reference as if fully set forth herein, under 35 U.S.C. §119(e). Cells of the immune system, such as T-cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243, the entire contents of which are hereby incorporated by reference as if fully set forth herein, under 35 U.S.C. §119(e)). The separated cells are stimulated with one or more of the immunoreactive peptides contained within a delivery vehicle, such as a microsphere, to provide antigen-specific T-cells. The population of tumor antigen-specific T-cells is then expanded using standard techniques and the cells are administered back to the patient.

In a further embodiment, syngeneic or autologous dendritic cells may be pulsed with peptides corresponding to at least an immunogenic portion of a peptide disclosed herein. The resulting antigen-specific dendritic cells may either be transferred into a patient, or employed to stimulate T-cells to provide antigen-specific T-cells which may, in turn, be administered to a patient. The use of peptide-pulsed dendritic cells to generate antigen-specific T-cells and the subsequent use of such antigen-specific T-cells to eradicate tumors in a murine model has been demonstrated by Cheever et al, Immunological Reviews, 157:177, 1997, the entire contents of which are hereby incorporated by reference as if fully set forth herein, under 35 U.S.C. §119(e).

Certain embodiments of the present invention are directed to T-cells or dendritic cells, isolated from a patient for use in immunotherapy. Certain embodiments are further directed to T-cell vaccines and dendritic cell vaccines that contain the T-cells and dendritic cells just described. Likewise, the dendritic cell and T-cell vaccines can be directed to a single epitope or to more than one epitope. Certain further embodiments are directed to methods of treating prostate cancer in a male animal by administering the dendritic cell and T-cell vaccines of the present invention to the patient to increase the immune response to the PSA-derived peptides. Additionally, vectors expressing the disclosed polynucleotides may be introduced into stem cells taken from the patient and clonally propagated in vitro for autologous transplant back into the same patient.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a prostate tumor protein generally correlate with an improved clinical outcome. Such immune responses may generally be evaluated using standard proliferation, cytotoxicity or cytokine assays, which may be performed using samples obtained from a patient before and after treatment.

Summary

Transgenic mice that express an HLA-DRB1*1501 chimeric construct and that are deficient for mouse class II genes were immunized with human PSA and had robust recall proliferative responses to the antigen. By screening a 20-mer peptide library that overlapped by 10 amino acids and spanned the entire mature secreted PSA sequence, two new 20-mer peptides $PSA_{171-190}$ and $PSA_{221-240}$ were identified that were immunogenic in vivo in DR2b Tg mice. The $PSA_{171-190}$ and $PSA_{221-240}$ epitopes were capable of stimulating human CD4 T-cells derived from patients with GP and prostate cancer that are HLA-DRB1*1501-positive and they were naturally processed from whole PSA by human APC. Of the 2 epitopes detected, $PSA_{221-240}$ proved to be immunodominant. This is first demonstration of HLA-DRB1*1501-restricted immunogenic peptides derived from whole PSA that is naturally processed and presented to T-cells. Other 13-mer immunogenic PSA-derived peptides were also identified.

Antigen processing in various mammalian cells is quite similar. Madsen et al. (11) showed that when the DR2b tg mice were also made transgenic for a human TCR that recognized a peptide from human myelin basic protein (MBP 84-102) the animals developed an MS-like disease showing that the same peptide from patients was presented in the mice. This provides strong evidence for the notion that peptides identified in DR2 mice vaccinated with human PSA will also be naturally processed from whole PSA in humans in vivo. Indeed, $PSA_{171-190}$ and $PSA_{221-240}$ specific T-cells were able to recognize whole PSA in an MHC-restricted manner showing that these peptides are naturally processed and presented by mouse and human APC.

Numerous data indicate that the majority of autoreactive peripheral blood T-cells are low affinity. This is particularly important for naturally processed peptides since T-cells recognizing these peptides with high affinity undergo negative selection in thymus in early life before most men develop prostate cancer. Both $PSA_{171-190}$ and $PSA_{221-240}$ peptides contained 9-mer core amino acid sequences with relatively low potential binding to HLA-DRB1*1501 (30% of the highest achievable score, ProPred program). However, both fragments demonstrated a low level of similarity to other human proteins when analyzed using PIR nonredundant reference protein database and peptide match program (17). It has been demonstrated recently for melanoma-derived antigens that epitopes with low similarity levels to the human proteome are preferred immunogenic epitopes (20). A low level of similarity is also important when a peptide is considered as a candidate for immunotherapy because it indicates that the probability of cross-reaction with other tissues after immunization with these peptides is low.

The generation of human antigen-specific CD4 T-cell lines from peripheral blood is aided by selecting donors that were exposed to the antigen in the past and have memory T-cells in peripheral circulation. In the experiments described herein this problem was addressed and overcome by utilizing a unique population of patients with GP that may manifest naturally the immune responses to prostatic antigens. Reliable and reproducible antigen-specific responses from T-cells required 3 or more IVS.

Peptide-class II tetramers (22) can be made from HLA-DRB1*1501 men with GP and normal donors. Tetramers for a peptide will only bind to T-cells that have a receptor for that specific peptide/mhc complex. Peptide-class II tetramers can be used to determine the response of a subject to vaccines using the PSA-derived antigens of the present invention. If the PSA-derived antigens have elicited an immune response, there will be T-cells in the subject's blood that are recognized by and bind to the Peptide-class II tetramers. It is also possible to diagnose prostate cancer by screening peripheral blood for T-cells that bind to peptide-class II tetramers of the PSA-derived antigens. Therefore another embodiment is directed to the use of PSA-derived peptide-MHC class II tetramers to diagnose prostate cancer by screening peripheral blood for T-cells that bind to peptide-class II tetramers of the PSA-derived antigens. The choice of the restriction element for the studies reported herein was in part dictated by our previous finding that GP is linked to HLA-DRB1*1501 allele in Caucasians (7). The induction of autoimmune responses to prostate antigens in prostate cancer patients with appropriate susceptible HLA type using the vaccines of the present invention has great clinical use since the prostate gland is not a vital organ beyond reproductive years. The establishment of CD4 T-cell lines specific to $PSA_{221-240}$ from peripheral blood of a patient with prostate cancer, as was reported above, also provides a new adoptive immunotherapy for prostate cancer patients, which can be applied to the other new PSA-derived immunogenic peptides identified here.

Genetic Vaccines

As was mentioned above, certain embodiments of this invention are directed to genetic vaccines using "minigenes" that are essentially naked DNA encoding one or more copies of the desired immunogenic PSA-derived peptide or peptides. Ulmer et al., Science 259:1745-1749, 1993 and reviewed by Cohen, Science 259:1691-1692, 1993, the entire contents of which are hereby incorporated by reference as if fully set forth herein, under 35 U.S.C. §119(e). The vaccine is typically injected into a host and the encoded peptide is then generated in vivo in the host. Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors. In general, a vector will contain an origin of replication functional in at least one organism, convenient restriction endonuclease sites and one or more selectable markers. Other elements will depend upon the desired use, and will be apparent to those of ordinary skill in the art. Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating polynucleotides into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific targeT-cell, to render the vector target specific. Targeting may also be accomplished using an antibody, by methods known to those of ordinary skill in the art. The uptake of naked polynucleotides, also called "minigenes," may be increased by coating the polynucleotides onto biodegradable beads, which are efficiently transported into the cells.

The polynucleotide sequences encoding the PSA-derived antigens of this invention can be expressed as single epitope minigenes or as linked epitopes in a string of beads configuration, such that a single peptide is produced containing multiple epitopes. The epitope can be expressed as a polyepitope, which consists of multiple repeats of the same epitope, with or without spacer amino acids flanking the epitope, or multi-epitope consisting of a combination of different epitopes. The epitopes could be assembled into either single peptide chain or expressed under separate promoters. This approach is widely used in the development of vaccines against cancer. Tine et all, Vaccine 2005 23:1085-1091, the entire contents of which are hereby incorporated by reference as if fully set forth herein, under 35 U.S.C. §119(e). Various mammalian expression vectors can be used to make the genetic vaccines of this invention, for example pVAX1 (Invitrogen Life Technologies) (Anwar et al Virology 2005 332: 66-77), pcDNA3 (Buchan et al J. Immunol. 2005, 174:6292-6298) or pCMVE (Biragyn at al, J. Immunol. 2001, 167: 6644-6653). Alternatively, replication-deficient or attenuated viruses could be used as an expression platform such as vaccinia virus, fowlpox virus (Tsang et al Clin Cancer Res 2005 11:1597-1607) or attenuated poxvirus canarypox (AL-VAC) (Tine et all, Vaccine 2005 23:1085-1091). The entire contents of the references in this paragraph are hereby incorporated by reference as if fully set forth herein, under 35 U.S.C. §119(e).

In another embodiment the genetic vaccine for MHC class II is designed as a chimera with the transmembrane and carboxyl terminal domains of the lysosome-associated membrane protein (LAMP) that is used to direct the antigen protein to the major histocompatibility class II (MHC class II) vesicular compartment of transfected antigen-presenting cells. Anwar et al., Virology 2005 332: 66-77, the entire contents of which are hereby incorporated by reference as if fully set forth herein, under 35 U.S.C. §119(e).

In another embodiment the potency of the genetic anti-cancer vaccine is enhanced by simultaneous expression of genes encoding costimulatory molecules such as CD80 (B7-1), CD54 (ICAM-1) and CD58 (LFA-3) as single genes or as a triad (TRICOM). Tsang et al 2005).

The minigenes having one or more of the PSA-derived peptide epitope(s) can also be designed and expressed as fusion proteins with molecules known to enhance anti-tumor immunity or target a particular subpopulation of antigen-presenting cells as was discussed above.

Prostate Cancer Therapy

In further aspects of the present invention, the pharmaceutical compositions and vaccines described herein may be used for immunotherapy of cancer, such as prostate cancer, in a patient. As to the vaccines, one or more of the immunogenic PSA-derived peptides of this invention (also including fusion proteins) is administered to stimulate the patient's own immune response to prostate tumor cells. Pharmaceutical compositions for treating cancer include the patient's own isolated T-cells that are specific for one or more of the immunogenic PSA-derived peptides or fusion proteins of this invention.

Within such methods, pharmaceutical compositions and vaccines are typically administered to a patient. As used herein, a "patient" refers to any warm-blooded male animal, preferably a human. A patient may be afflicted with prostate cancer, or may be free of detectable disease. Accordingly, the above vaccines may be used to prevent the development of prostate cancer or to treat a patient afflicted with prostate cancer. Prostate cancer may be diagnosed using criteria generally accepted in the art. Vaccines may be administered either prior to or following surgical removal of primary tumors and/or treatment such as administration of radiotherapy or conventional chemotherapeutic drugs.

If being used prophylactically, the vaccines of the present invention should be administered to those at high risk of developing prostate cancer, including African American men and men with a positive family history of prostate cancer. Routes and frequency of administration, as well as dosage, will vary from individual to individual, and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 3-24 week period. Preferably, 4 doses are administered, at an interval of 3 months, and booster administrations may be given periodically thereafter. Alternate protocols may be appropriate for individual patients. This is often referred to as a prime and boost vaccine regimen. In one embodiment, the prime and boost vaccines are the same. In another embodiment, a first vaccine is used for the prime and a second different vaccine is used for the boost.

A suitable dose is an amount of peptide or polynucleotide or activated T-cells that is effective to raise an immune response (cellular and/or humoral) against prostate tumor cells in a treated patient. A suitable immune response is at least 10-50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, the amount of peptide present in a dose (or produced in situ by the polynucleotides molecule in a dose) ranges from about 1 pg/kg to about 1 mg/kg of host. Suitable doses will vary with the size of the patient. A variety of routes of administration for the antibodies and immunoconjugates may be used. Typically, administration will be intravenous, intramuscular, subcutaneous or in the bed of a resected tumor. It will be evident that the precise dose and schedule of the antibody/immunoconjugate will vary depending upon the antibody used, the antigen density on the tumor, and the rate of clearance of the antibody.

Fusion Proteins Containing PSA-Derived Peptides

The PSA-derived peptides listed in Table 1 were chemically synthesized by the Biopolymer Core Facility, University of Maryland (Baltimore, Md.) and purified to >90% by reversed-phase HPLC. The molecular weights were confirmed by mass spectrometry. Peptides within the scope of the present invention can be synthesized by any method known in the art. For example, such peptides may be synthesized using any of the commercially available solid-phase techniques, such as the Merrifield solid-phase synthesis method, where amino acids are sequentially added to a growing amino acid chain. See Merrifield, J. Am. Chem. Soc. 85:2149-2146, 1963. Equipment for automated synthesis of peptides is commercially available from suppliers such as Applied BioSystems, Inc. (Foster City, Calif.), and may be operated according to the manufacturer's instructions.

Within certain specific embodiments, a peptide may be a fusion protein. In one embodiment the fusion protein has multiple different PSA-derived peptides as described herein. Alternatively, it can include one PSA-derived peptide as described herein and at least one other protein including another antigen or immune stimulant. A fusion protein generally comprises at least one DNA molecule encoding a PSA-derived peptide and one or more additional immunogenic or immune stimulatory sequences, which are joined via a peptide linkage into a single amino acid chain. The sequences may be joined directly (i.e., with no intervening amino acids) or may be joined by way of a linked sequence (e.g., Gly-Cys-Gly) that does not significantly diminish the immunogenic properties of the component peptides. Other embodiments are directed to the use of fusion proteins that have one or more of the PSA-derived peptides of the present invention as vaccines for prostate cancer. Immune response enhancers suitable for inclusion in the fusion peptides include for example interleukin IL-12 (IL12) (Li et al. Hybridoma and Hybridomics, Vol. 23, No. 1, 2004, 1-10), granulocytes-macrophage colony-stimulating factor (GM-CSF) (Lima et al, Vaccine 23, (2005), 1273-83, Elsevier Ltd.), chemokines and defensins (β2-defensin, β-3 defensin, MIP3α) (Biragin et al 2001) or other adjuvant molecules such as fragment C (FrC) of tetanus toxin ((Buchan et al J. Immunol. 2005, 174:6292-6298)) or heat shock protein 70-like protein 1 (Hsp70L1) (Wu, Y., et al., Cancer Res. 2005, Vol. 65 (11), 4947-54).

Fusion proteins are also provided that comprise one or more PSA-derived peptides of the present invention together with an unrelated immunogenic protein. Preferably the immunogenic protein is capable of eliciting a recall response. Examples of such proteins include tetanus, tuberculosis and hepatitis proteins (see, for example, Stoute et al. New Engl. J. Med., 336:86-91, 1997). Wu, Y., et al., Cancer Res. 2005, Vol. 65 (11), 4947-54, the entire contents of the references in this paragraph are hereby incorporated by reference as if fully set forth herein, under 35 U.S.C. §119(e).

Fusion proteins may generally be prepared using standard techniques. For example, a fusion protein may be prepared recombinantly. Briefly, DNA sequences encoding the peptide components may be assembled separately, and ligated into an appropriate expression vector. The 3' end of the DNA sequence encoding one peptide component is ligated, with or without a peptide linker, to the 5' end of a DNA sequence encoding the second peptide component so that the reading frames of the sequences are in phase. This permits translation into a single fusion protein that retains the biological activity of both component peptides.

A peptide linker sequence may be employed to separate the first and the second peptide components by a distance sufficient to ensure that each peptide folds into its secondary and tertiary structures. Such a peptide linker sequence may be incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second peptides; and (3) the lack of hydrophobic or charged residues that might react with the peptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second peptides have non-essential N-terminal amino acid regions that can be used to separate the functional domains and prevent steric interference.

Polynucleotide Synthesis

The polynucleotides can be made by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). The percent identity may be readily determined by comparing sequences using computer algorithms well known to those of ordinary skill in the art, such as Megalign, using default parameters. Certain variants are substantially homologous to a native gene, or a portion or complement thereof. Such polynucleotide variants are capable of hybridizing under moderately stringent conditions to a naturally occurring DNA sequence encoding a native prostate tumor protein (or a complementary sequence). Suitable moderately stringent conditions include prewashing in a solution of 5.times.SSC, 0.5% SDS, 1.0 mM EDTA (pH 8.0); hybridizing at 50.degree. C.-65.degree. C., 5.times.SSC, overnight; followed by washing twice at 65.degree. C. for 20 minutes with each of 2×, 0.5× and 0.2.times.SSC containing 0.1% SDS).

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the peptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants containing substitutions may also (or alternatively) be modified by, for example, the deletion or addition of amino acids that have minimal influence on the immunogenicity, secondary structure and hydropathic nature of the peptide.

The ligated polynucleotide sequences are operably linked to suitable transcriptional or translational regulatory elements. The regulatory elements responsible for expression of polynucleotide are located only 5' other polynucleotide sequence encoding the first peptides. Similarly, stop codons required to end translation and transcription termination signals are only present 3' to the polynucleotide sequence encoding the second peptide.

Embodiments of the present invention encompass immunogenic PSA-derived polynucleotides and variants thereof. Polynucleotide variants may contain one or more substitutions, additions, deletions and/or insertions such that the therapeutic, antigenic and/or immunogenic properties are not substantially diminished, relative to the immunogenic PSA-derived polynucleotide of which it is a variant. Such modifications may be readily introduced using standard mutagenesis techniques, such as oligonucleotide directed site-specific mutagenesis as taught, for example, by Adelman et al. (DNA, 2:183, 1983). Preferably, the antigenicity or immunogenicity of a peptide variant is not substantially diminished.

It will be appreciated by those of ordinary skill in the art that, as a result of the degeneracy of the genetic code, there are many nucleotide sequences that encode a peptide as described herein. Some of these polynucleotides bear minimal homology to the nucleotide sequence of any native gene. Nonetheless, polynucleotides that vary due to differences in codon usage are specifically contemplated by the present invention.

The effect on the immunogenicity of the encoded peptide may generally be assessed as described herein. Variants preferably exhibit at least about 70% identity, more preferably at least about 80 preferably at least about 80%, 85%, 86%, 87%, 88%, 89% identity and most preferably at least about 90%, 91%, 92%, 93%, 94%, 95%, 96%, 97%, 98% or 99% identity to a polynucleotide sequence that encodes a native prostate tumor protein or a portion thereof. The present invention includes variants that have the core epitope, but are less than 80% homologous, as long as immunogenicity is substantially retained. Some variants are listed in Tables 2-5. The percent identity may be readily determined by comparing sequences using computer algorithms well known to those of ordinary skill in the art, such as Megalign, using default parameters. Certain variants are substantially homologous to the immunogenic PSA-derived polynucleotide of which it is a variant. Such polynucleotide variants are capable of hybridizing under moderately stringent conditions to a naturally occurring DNA sequence encoding the immunogenic PSA-derived polynucleotide of which it is a variant (or a complementary sequence). Suitable moderately stringent conditions include prewashing in a solution of 5.times.SSC, 0.5% SDS, 1.0 mM EDTA (pH 8.0); hybridizing at 50.degree. C.-65.degree. C., 5.times.SSC, overnight; followed by washing twice at 65.degree. C. for 20 minutes with each of 2×, 0.5× and 0.2.times.SSC containing 0.1% SDS).

Determination of the Minimal PSA Peptide Binding Motif.

The minimal epitopes for $PSA_{171-190}$ and $PSA_{221-240}$ will be determined by synthesis of peptide epitopes with sequential single truncations from the carboxy- and amino-terminus until critical deletions at each end (which ablate the response of human CD4 T-cell lines specific to the 20-mer peptide) are identified. Variants for use in the vaccines of the present invention are outlined in the Tables 2 and 3. The peptides shorter than 9-mers are unlikely to bind to the MHC class II molecule. The readout for these experiments will be secretion of IFN-γ by CD4 T-cell lines specifically recognizing the 20-mer sequences. We have already produced these lines as described herein and in Klyushnenko, E. N., et al., Clin. Cancer Res. 2005; 11(8) 2853-61, Apr. 15, 2005, the entire contents of which are hereby incorporated by reference as if fully set forth herein, under 35 U.S.C. §119(e).

TABLE 2

Proposed truncated peptide variants derived from peptide $PSA_{171-190}$

| C-terminus truncates | | N-terminus truncates | |
|---|---|---|---|
| Position (length) | Sequence | Position (length) | Sequence |
| 171-189 (19) SEQ ID NO. 13 | LQCVDLHVISN DVCAQVHP | 172-190 (19) SEQ ID NO. 80 | QCVDLHVISNDVC AQVHP |
| 171-188 (18) SEQ ID NO. 14 | LQCVDLHVISN DVCAQVH | 173-190 (18) SEQ ID NO. 81 | CVDLHVISNDVCA QVHP |
| 171-187 (17) SEQ ID NO. 15 | LQCVDLHVISN DVCAQV | 174-190 (17) SEQ ID NO. 82 | VDLHVISNDVCAQ VHP |
| 171-186 (16) SEQ ID NO. 16 | LQCVDLHVISN DVCAQ | 175-190 (16) SEQ ID NO. 83 | DLHVISNDVCAQV HP |
| 171-185 (15) SEQ ID NO. 17 | LQCVDLHVISN DVCA | 176-190 (15) SEQ ID NO. 84 | LHVISNDVCAQVH P |
| 171-184 (14) SEQ ID NO. 18 | LQCVDLHVISN DVCA | 177-190 (14) SEQ ID NO. 85 | HVISNDVCAQVHP |
| 171-183 (13) SEQ ID NO. 19 | LQCVDLHVISN DV | 178-190 (13) SEQ ID NO. 86 | VISNDVCAQVHP |
| 171-182 (12) SEQ ID NO. 20 | LQCVDLHVISN D | 179-190 (12) SEQ ID NO. 87 | ISNDVCAQVHP |
| 171-181 (11) SEQ ID NO. 21 | LQCVDLHVISN | 180-190 (11) SEQ ID NO. 88 | SNDVCAQVHP |
| 171-180 (10) SEQ ID NO. 22 | LQCVDLHVIS | 181-190 (10) SEQ ID NO. 89 | NDVCAQVHP |
| 171-179 (9) SEQ ID NO. 23 | LQCVDLHVI | 182-190 (9) SEQ ID NO. 90 | DVCAQVHP |

TABLE 3

PROPOSED TRUNCATED PEPTIDES DERIVED FROM PEPTIDE $PSA_{221-240}$

| C-terminus truncates | | N-terminus truncates | |
|---|---|---|---|
| Position (length) | Sequence | Position (length) | Sequence |
| 221-239 (19) SEQ ID NO. 24 | GVLQGITSWGSE PCALPER | 222-240 (19) SEQ ID NO. 35 | VLQGITSWGSE PCALPERP |
| 221-238 (18) SEQ ID NO. 25 | GVLQGITSWGSE PCALPE | 223-240 (18) SEQ ID NO. 36 | LQGITSWGSEP CALPERP |

TABLE 3-continued

PROPOSED TRUNCATED PEPTIDES DERIVED FROM
PEPTIDE PSA$_{221-240}$

| C-terminus truncates | | N-terminus truncates | |
|---|---|---|---|
| Position (length) | Sequence | Position (length) | Sequence |
| 221-237 (17) SEQ ID NO. 26 | GVLQGITSWGSE PCALP | 224-240 (17) SEQ ID NO. 37 | QGITSWGSEPC ALPERP |
| 221-236 (16) SEQ ID NO. 27 | GVLQGITSWGSE PCAL | 225-240 (16) SEQ ID NO. 38 | GITSWGSEPCA LPERP |
| 221-235 (15) SEQ ID NO. 28 | GVLQGITSWGSE PCA | 226-240 (15) SEQ ID NO. 39 | ITSWGSEPCAL PERP |
| 221-234 (14) SEQ ID NO. 29 | GVLQGITSWGSE PC | 227-240 (14) SEQ ID NO. 40 | TSWGSEPCALP ERP |
| 221-233 (13) SEQ ID NO. 30 | GVLQGITSWGSE P | 228-240 (13) SEQ ID NO. 41 | SWGSEPCALPE RP |
| 221-232 (12) SEQ ID NO. 31 | GVLQGITSWGSE | 229-240 (12) SEQ ID NO. 42 | WGSEPCALPER P |
| 221-231 (11) SEQ ID NO. 32 | GVLQGITSWGS | 230-240 (11) SEQ ID NO. 43 | GSEPCALPERP |
| 221-230 (10) SEQ ID NO. 33 | GVLQGITSWG | 231-240 (10) SEQ ID NO. 44 | SEPCALPERP |
| 221-229 (9) SEQ ID NO. 34 | GVLQGITSW | 232-240 (9) SEQ ID NO. 45 | EPCALPERP |

Determination of the Optimal PSA Peptide Binding Motif.

Once the minimal residue core peptide is identified, we will add back flanking residues of the original peptide until optimal length is achieved as determined by maximum secretion of IFN-γ by CD4 T-cell lines specifically recognizing the 20-mer sequences. Based on the data of Wucherpfenning et al., the prediction of the ProPed software Singh, et al. and our data (FIG. 8 in Clin Cancer Research) the likely core sequence represents the 9-mers PSA$_{171-179}$ and PSA$_{223-231}$, which 9-mers are an embodiment of the present invention and can be used in vaccines for prostate cancer. Wucherpfennig, K. W., A. Sette, S. Southwood, C. Oseroff, M. Matsui, J. L. Strominger, and D. A. Hafler. 1994, and Singh, H. and G. P. Raghava. 2001. ProPred: prediction of HLA-DR binding sites. *Bioinformatics*. 17:1236-1237, the entire contents of which are hereby incorporated by reference as if fully set forth herein, under 35 U.S.C. §119(e). Structural requirements for binding of an immunodominant myelin basic protein peptide to DR2 isotypes and for its recognition by human T-cell clones are described in *J. Exp. Med*. 179:279-290, the entire contents of which are hereby incorporated by reference as if fully set forth herein, under 35 U.S.C. §119(e).

We will synthesize peptides with 1, 2 or 3 amino acids added from either N-terminus or C-terminus end or from both ends of the 9-mer sequence. The example of such additions based on the 9-mer sequence PSA$_{223-231}$ within 20-mer peptide PSA$_{221-240}$ is outlined in the Table 4. We expect that peptides of 12-15 amino acids will be optimal. Optimal epitopes identified in vitro in human cultures will be tested for the immunogenicity in vivo in DR2b tg mice.

TABLE 4

| N-terminus additions | C-terminus additions | | | |
|---|---|---|---|---|
| | No addition | +1 aa | +2 aa | +3 aa |
| No addition | LQGITSWGS (223-231) [9-mer] SEQ ID NO. 46 | LQGITSWGSE (223-232) [10-mer] SEQ ID NO. 50 | LQGITSWGSEP (223-233) [11-mer] SEQ ID NO. 54 | LQGITSWGSE PC (223-234) [12-mer] SEQ ID NO. 58 |
| +1 aa | VLQGITSWGS (222-231) [10 mer] SEQ ID NO. 47 | VLQGITSWGS E (222-232) [11-mer] SEQ ID NO. 51 | VLQGITSWGSEP (222-233) [12-mer] SEQ ID NO. 55 | VLQGITSWGS EPC (222-234) [13-mer] SEQ ID NO. 59 |
| +2 aa | GVLQGITSW GS (221-231) [11-mer] SEQ ID NO. 48 | GVLQGITSW GSE (221-232) [12-mer] SEQ ID NO. 52 | GVLQGITSWGSE P (221-233) [13-mer] SEQ ID NO. 56 | GVLQGITSW GSEPC (221-234) [14-mer] SEQ ID NO. 60 |
| +3 aa | NGVLQGITS WGS (220-231) [12-mer] SEQ ID NO. 49 | NGVLQGITS WGSE (220-232) [13-mer] SEQ ID NO. 53 | NGVLQGITSWGS EP (220-233) [14-mer] SEQ ID NO. 57 | NGVLQGITS WGSEPC (220-234) [15-mer] SEQ ID NO. 61 |

Search for the Agonist HLA-DRB1*1501-Restricted PSA Peptides

After the minimal core epitope and flanking residues are determined, amino acid substitutions that improve predicted binding score will be made within core epitope based on the virtual matrix for HLA-DRB1*1501 using ProPred software[2] as shown in Table 5. To ensure that selected peptides are able to stimulate the immune responses in human cultures, CD4 T-cell lines specific to the optimal unmodified and modified epitopes will be developed by multiple stimulations of CD4 T-cells from HLA-DRB1*1501 patients pre-selected for the responsiveness to 20-mer peptides. Three best scoring modified peptides will be tested for immunogenicity in vivo in DR2b tg mice. Another embodiment is directed to the variants of PSA-derived peptides set forth in Table 5.

TABLE 5

Amino Acid SEQ ID NO. substitutions and predicted MHC Class II binding results for the core sequences of $PSA_{171-191}$ and $PSA_{221-241}$ based on A virtual matrix for HLA-DRB1*1501

| Peptide sequence | Modify | Predicted binding score | Peptide sequence | Modify | Predicted binding score |
|---|---|---|---|---|---|
| PSA171-179 LQCVDLHVI | None | 2.9 | PSA223-231 LQGITSWGS | none | 2.9 |
| LRCVDLHVI SEQ ID NO. 63 | p2 Q→R | 3.9 | LRGITSWGS SEQ ID NO. 70 | p2 Q→R | 3.9 |
| LVCVDLHVI SEQ ID NO. 64 | p2 Q→V | 3.8 | LQIITSWGS SEQ ID NO. 71 | p3 G→I | 4.2 |
| LQIVDLHVI SEQ ID NO. 65 | p3 C→I | 4.4 | LQLITSWGS SEQ ID NO. 72 | p3 G→L | 3.7 |
| LQCYDLHVI SEQ ID NO. 66 | p4 V→Y | 5.2 | LQGYTSWGS SEQ ID NO. 73 | p4 I→Y | 4.8 |
| LQCFDLHVI SEQ ID NO. 67 | p4 V→F | 5.1 | LQGFTSWGS SEQ ID NO. 74 | p4 I→F | 4.7 |
| LQCVDRHVI SEQ ID NO. 68 | p6 L→R | 3.7 | LQGITRWGS SEQ ID NO. 75 | p6 S→R | 3.4 |
| LQCVDLLVI SEQ ID NO. 91 | p7 H→L | 4.2 | LQGITSLGS SEQ ID NO. 76 | p7 W→L | 4.2 |
| LQCVDLMVI SEQ ID NO. 92 | p7 H→M | 4.0 | LQGITSMGS SEQ ID NO. 77 | p7 W→M | 4.0 |
| | | | LQGITSFGS SEQ ID NO. 78 | p7 W→F | 3.7 |
| | | | LQGITSWGL SEQ ID NO. 79 | p9 S→L | 4.5 |

Carriers, Routes of Administration, Formulations

The A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873, 088).

A variety of routes of administration for the antibodies and immunoconjugates may be used. Typically, administration is intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

The PSA-derived peptides and the polynucleotides encoding them together with (optionally) binding agents may be incorporated into pharmaceutical compositions or vaccines. Pharmaceutical compositions comprise one or more such compounds and a physiologically acceptable carrier. Vaccines may comprise one or more such compounds and one or more non-specific or specific immune response enhancers. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated). Pharmaceutical compositions and vaccines within the scope of the present invention may also contain other compounds, which may be biologically active or inactive. For example, one or more immunogenic portions of other tumor antigens may be present, either incorporated into a fusion peptide or as a separate compound within the composition or vaccine.

A pharmaceutical composition or vaccine may contain polynucleotides encoding one or more of the PSA-derived peptides described above, such that the peptide is generated in situ. As noted above, the polynucleotides may be present within any of a variety of delivery systems known to those of ordinary skill in the art, including nucleic acid expression systems, bacteria and viral expression systems. Appropriate nucleic acid expression systems contain the necessary polynucleotide sequences for expression in the patient (such as a suitable promoter and terminating signal).

Bacterial delivery systems involve the administration of a bacterium (such as Bacillus-Calmette-Guerrin) that expresses an immunogenic portion of the peptide on its cell surface. In an embodiment, the polynucleotides may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., PNAS 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., PNAS 91:215-219, 1994; Kass-Eisler et al., PNAS 90:11498-11502, 1993; Guzman et al., Circulation 88:2838-2848, 1993; and Guzrnan et al., Cir. Res. 73:1202-1207, 1993, the entire contents of which are hereby incorporated by reference as if fully set forth herein, under 35 U.S.C. §119(e). Techniques for incorporating polynucleotides into such expression systems are well known to those of ordinary skill in the art.

While any suitable carrier known to those of ordinary skill in the art may be employed in the pharmaceutical compositions of this invention, the type of carrier will vary depending on the mode of administration. Compositions of the present invention may be formulated for any appropriate manner of administration including, for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, peptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

The compositions described herein may be administered as part of a sustained release formulation (i.e., a formulation such as a capsule or sponge that causes a slow release of compound following administration). Such formulations may generally be prepared using well known technology and administered by, for example, oral, rectal or subcutaneous implantation, or by implantation at the desired target site. Sustained-release formulations may contain a peptide or polynucleotide of the present invention dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

EXAMPLES

Example 1

Immunizations and In Vitro Proliferative Assay

Peptides: peptides were synthesized at the Biopolymer Core Facility, University of Maryland (Baltimore, Md.) and purified to >90% by reversed-phase HPLC. The molecular weights were confirmed by mass spectrometry. Peptides within the scope of the present invention can be synthesized by any method known in the art.

HLA-DR2b tg mice bearing chimeric MHC class II molecules consisting of the α1 and β1 sequences of HLA-DRA1*0101 and HLA-DRB1*1501 and the α2 and β2 domains of IEα and IEβ, respectively were developed as previously described (12; 13). Transgenic offspring were backcrossed twice to the MHC class II knock out mouse, MHCII$^{Δ/Δ}$ resulting in deletion of all normal mouse class II molecules (14), hence T-cell responses in these mice are restricted exclusively by HLA-DRB1*1501. The expression of HLA-DR on DR2b tg mice were analyzed by flow cytometry using anti-pan-DR PE mAb (Sigma, St. Louis, Mo.). The mice did not express the endogenous mouse Class II molecules as determined by staining with anti-I-A/E FITC mAb (BD Bioscience Pharmingen, San Diego, Calif.) (10). HLA-DR2b tg male mice between 8 and 12 weeks of age were immunized subcutaneously (s.c.) at four sites on the flanks with 0.2 ml of an emulsion comprised of 50 μg PSA purified from human seminal fluid (Fitzgerald Industries International, Concord, Mass.) or 200 μg peptide in complete Freund's adjuvant (CFA) containing 400 μg *Mycobacterium tuberculosis* H37RA (Difco, Detroit, Mich.).

Spleens and inguinal lymph nodes from HLA-DR2b tg mice were recovered 9-11 days after immunization and processed into single-cell suspensions. T-cell proliferation responses were assessed by plating 4×10$^5$ cells per well in a 96-well flat-bottom tissue culture plate in triplicate with stimulation media alone (control) or in the presence of antigens in 2% fetal bovine serum (FBS)-containing RPMI 1640 medium supplemented with 0.05 mM 2-Mercaptoethanol (ME), 2 mM L-glutamine, 1 mM sodium pyruvate, 100 μg/ml penicillin G, 100 μg/ml streptomycin (InVitrogen GIBCO, Carlsbad, Calif.). Cultures were incubated 72 hr at 37° C. in 7% $CO_2$. Wells were pulsed for the final 18 hr with 0.5 μCi per well [$^3$H] thymidine (Amersham, Arlington Heights, Ill.). The cells were harvested onto glass fiber filters and [$^3$H] thymidine uptake was measured using a liquid scintillation counter (1205 Betaplate; Wallac, Turku, Finland). Mean counts per minute (CPM)±SD were calculated for triplicate wells.

Example 2

Patients and HLA Typing

Five HLA-DRB1*1501+ patients with GP were identified through clinical practice at the VAMHCS and University of Maryland. Patients underwent automated leukopheresis to obtain PBMC in the University of Maryland Cancer Center apheresis unit under IRB-approved protocol. PBMC were separated by centrifugation on LSM Lymphocyte Separation Medium (ICN Biomedicals, Inc., Aurora, Ohio) and cryopreserved. HLA typing at intermediate resolution and high resolution typing of DR15 alleles was determined at the American Red Cross National Histocompatibility Laboratory at University of Maryland.

Example 3

Development of Human CD4 T-Cell Lines Specific for PSA Peptide and Functional Characterization of Human Peptide-Specific T-Cell Lines CD4 T-cells were prepared from PBMC by negative selection using human CD4 T-cells Negative Isolation Kit (Dynal Biotech, Inc., Lake Success, N.Y.). Irradiated (3,300 rad) autologous PBMC were used as antigen-presenting cells (APC). CD4 T-cells were added at $1\times10^6$ cells/well, irradiated PBMC at $2\times10^6$ cells/well, peptides at 20 μg/ml. Cells were incubated at 2 ml/well in 24-well plates in Iscove's Modified Dulbecco's media with following supplements: 2 mM L-glutamine, 0.1 mM MEM non-essential amino acids, 1 mM MEM sodium pyruvate, 100 U/ml penicillin, 100 μg/ml streptomycin, 0.05 mM 2-ME (all reagents from InVitrogen, Carlsbad, Calif.), 5% human AB serum (Gemini Bio-Products, Woodland, Calif.) and rhIL-7 at 10 ng/ml (PeproTech, Rocky Hill, N.J.) in a humidified 37° C., 5% $CO_2$. Recombinant human rIL-2 (Chiron Corp., Emeryville, Calif.) was added at 30 IU/ml on day 2. Media containing IL-2 and IL-7 was replaced twice a week. Cells were re-stimulated every 14 days. The phenotype of surface markers expressed by T-cell lines was determined by flow cytometry using anti-CD4-FITC/anti-CD8-PE, anti-TcR α/β-FITC and IgG2a-FITC/IgG2a-PE mAbs (Caltag Laboratories, Burlingame, Calif.).

CD4 T-cells were taken to the assay at resting stage, 2-3 weeks after the exposure to antigen in a previous stimulation cycle, washed 3 times with culture media to remove cytokines, and plated into round-bottom 96-well tissue culture plates at 20,000 cells/well. Autologous PBMC were irradiated at 3,300 rad and added at 50,000 cells/well. Peptides or whole PSA were added at different concentrations (5-40 μg/ml). HEK 293 cell line expressing PSA was prepared by transfection of parental cell line with pSecTag2/PSA plasmid (InVitrogen). Cells transfected with pSecTag2/Hygro/A plasmid served as a negative control. PSA concentration was determined in culture supernatants by ELISA as described previously (9). To generate dendritic cells (DC), CD14+ cells (>95% pure) were prepared from PBMC by negative selection using Monocyte Negative Isolation kit (Dynal Biotech Inc.). Immature DC were cultured in the presence of rhIL-4 and rhGM-CSF (PeproTech) at 100 ng/ml each for 7 days, half of the media with fresh cytokines was replaced on day 4. To ensure optimal antigen uptake and processing, PSA or cell lysates were added at different concentrations to immature DC on day 4 after initiation of DC culture for 6-8 hr followed by incubation with rhTNFα (30 ng/ml) and rhIFNα (50 U/ml) (R&D Systems, Inc., Minneapolis, Minn.) for the remaining three days (15). The phenotype of mature DC was assessed by staining with anti-CD14 FITC (<1%), anti-CD83 PE (18-22%), anti-CD80 PE (13-25%), anti-HLA-DR PE (70-80%) and anti-CD86 FITC (98%) (all mAbs from Pharmingen). DC were harvested by gentle pipetting, washed 4 times to remove cytokines and added at 5,000 cells per well without irradiation. Monoclonal antibodies W6/32 (anti-HLA A,B,C), L243 (anti-HLA-DR) and IA14 (IgG2a) (American Type Culture Collection, Manassas, Va.) for blocking studies were produced by culturing hybridoma cells and purified from conditioned culture supernatant using protein A/G columns (Pierce Biotechnology Inc., Rockford, Ill.) and were added at 5-10 μg/ml. BLC cell line expressing DR2b (DRB1*1501) and parental BLC line were kindly provided by Dr. W. Kwok, University of Washington, Seattle (16). The lines were maintained in complete Iscove's Modified Dulbecco's media (supplemented with 2 mM L-glutamine, 0.1 mM MEM non-essential amino acids, 1 mM MEM sodium pyruvate, 100 U/ml penicillin, 100 μg/ml streptomycin and 10% FBS). BLC-DR2b line was cultured in the presence of G418 (InVitrogen) at 1 mg/ml. HLA type of BLC lines was determined by PCR-based typing using Micro SSP™ Generic HLA Class II DNA typing trays, the expression of HLA-DR1501 in BLC-DR2b line was confirmed using Micro SSP™ Allele-specific HLA Class II DNA typing trays—DRB1*15 (One Lambda, Inc., Canoga Park, Calif.). Cells were washed twice before mixing with T-cells, irradiated at 10,000 rad and added at 10,000 cells/well. Cultures were incubated for 48 hr. IFNγ secretion was measured in culture supernatants by ELISA using a pair of capture and biotinylated detecting mAbs (/Pierce/Endogen) as described earlier (9). To determine the level of DNA synthesis, [$^3$H] Thymidine (Amersham, specific activity 5 Ci/mmol,) was added at 1 μCi/well for additional 18 hr. Cultures were harvested using a Mach III M 96 well cell harvester (TOMTEC, Hamden, Conn.). Isotope incorporation was determined using a Wallac 1450 MicroBeta Trilux liquid scintillation counter (EG&G WALLAC, Turku, Finland).

Peptides may be prepared using any of a variety of well known techniques. Recombinant peptides encoded by polynucleotide sequences as described above may be readily prepared from the polynucleotide sequences using any of a variety of expression vectors known to those of ordinary skill in the art. Expression may be achieved in any appropriate host cell that has been transformed or transfected with an expression vector containing a polynucleotide molecule that encodes a recombinant peptide. In the case of the mini-gene therapy, the host is the patient receiving the mini-gene preferably by intramuscular injection.

What is claimed is:

1. An isolated DNA molecule encoding a prostate-specific antigen-derived peptide, wherein the isolated DNA molecule comprises a coding region consisting of a nucleotide sequence selected from the group consisting of SEQ ID NOs: 1, 3, 5, 7, 9 and 11.

2. The isolated DNA molecule of claim 1, wherein the coding region is operably linked to a promoter that drives expression in a host cell and the DNA molecule and promoter are incorporated into a DNA construct.

3. The isolated DNA molecule of claim 2, further comprising a second different coding region encoding a second different prostate-specific antigen-derived peptide, which second coding region consists of a nucleotide sequence selected from the group consisting of SEQ ID NOs: 1, 3, 5, 7, 9 and 11.

4. The isolated DNA molecule of claim 3, wherein the first and second coding regions are under the control of the same promoter.

5. The isolated DNA molecule of claim 3, wherein the first and second coding regions are under the control of different promoters.

6. A genetic vaccine comprising a DNA construct comprising an isolated DNA molecule encoding a prostate-specific antigen-derived peptide, wherein the isolated DNA molecule comprises a coding region consisting of a nucleotide sequence selected from the group consisting of SEQ ID NOs: 1, 3, 5, 7, 9 and 11, wherein the isolated DNA molecule is operably linked to a promoter that drives expression in a host cell.

* * * * *